United States Patent
Quinet et al.

(10) Patent No.: US 6,333,167 B1
(45) Date of Patent: Dec. 25, 2001

(54) METHODS AND REAGENTS FOR IDENTIFYING INHIBITORS OF PROTEOLYSIS OF MEMBRANE-ASSOCIATED PROTEINS

(75) Inventors: Elaine M. Quinet; David J. Shuey, both of Princeton, NJ (US)

(73) Assignee: American Home Products Corp., Parsippany, NJ (US)

(*) Notice: Subject to any disclaimer, the term of this patent is extended or adjusted under 35 U.S.C. 154(b) by 0 days.

(21) Appl. No.: 09/522,666

(22) Filed: Mar. 10, 2000

(51) Int. Cl.$^7$ ...................................................... C12Q 1/37
(52) U.S. Cl. .............................. 435/23; 435/23; 435/219; 435/350; 435/395; 435/320.1; 435/254.2; 435/325; 435/348; 435/349; 530/350; 536/23.4
(58) Field of Search ................................... 435/4, 23, 219, 435/350, 395, 320.1, 254.2, 325, 348, 349; 536/23.4; 530/350

(56) References Cited

U.S. PATENT DOCUMENTS

| | | | |
|---|---|---|---|
| 5,589,392 | 12/1996 | Short | ................................. 435/320.1 |
| 5,776,689 | 7/1998 | Karin et al. | ................................. 435/6 |

OTHER PUBLICATIONS

Steiner et al. An in vivo assay for the identification of target proteases which cleave membrane–associated substrates. FEBS Lett. 1999, vol. 463, pp. 245–249, 1999.*

Aronheim, et al. "Isolation of an AP–1 Repressor by a Novel Method for Detecting Protein–Protein Interactions" (1997) *Mol. Cell. Biol.* 17(6):3094–3102.

Boizard, et al. "Obesity–related Overexpression of Fatty–acid Synthase Gene in Adipose Tissue Involves Sterol Regulatory Element–binding Protein Transcription Factors" (1998) *J. Biol. Chem.* 273:29164–29171.

Briggs, et al. "Nuclear Protein That Binds Sterol Regulatory Element of Low Density Lipoprotein Receptor Promoter" (1993) *J. Biol. Chem.* 268:14490–14496.

Broder, et al. "The Ras recruitment system, a novel approach to the study of protein–protein interactions" (1998) *Curr. Biol.* 8(20):1121–1124.

Brown and Goldstein, "The SREBP Pathway: Regulation of Cholesterol Metabolism by Proteolysis of a Membrane–Bound Transcription Factor" (1997) *Cell* 89:331–340.

Buss, et al. "The Six Amino–Terminal Amino Acids of p60$^{src}$ Are Sufficient To Cause Myristylation of p21$^{v-ras}$" (1988) *Mol. Cell. Biol.* 8:3960–3963.

Capell, et al. "The Proteolytic Fragments of the Alzheimer's Disease–associated Presenilin–1 Form heterodimers and Occur as a 100–150–kDa Molecular Mass Complex" (1998) *J. Biol. Chem.* 273:3205–3211.

Espenshade, et al. "Autocatalytic Processing of Site–1 Protease removes Propeptide and Permits Cleavage of Sterol Regulatory Element–binding Proteins" (1999) *J. Biol. Chem.* 274:22795–22804.

Hancock, et al. "A CAAX or a CAAL motif and a second signal are sufficient for plasma membrane targeting of ras proteins" (1990) *EMBO J.* 10:4033–4039.

Hartman, et al. "Predicting the orientation of eukaryotic membrane–spanning proteins" (1989) *Proc. Natl. Acad. Sci. USA* 86:5786–5790.

Hua, et al. "Regulated Cleavage of Sterol Regulatory Element Binding Proteins Requires Sequences on Both Sides of the Endoplasmic Reticulum Membrane" (1996) *J. Biol. Chem.* 271:10379–10384.

Kalderon, et al. "A Short Amino Acid Sequence Able to Specify Nuclear Location" (1984) *Cell* 39:499–509.

Lamb, B.T. "Presenilins, amyloid–β and Alzheimer's disease" (1997) *Nature Med.* 3:28–29.

Lecureux, L.W. and Wattenburg, B.W. "The regulated degradation of a 3–hydroxy–3–methylglutaryl–coenzyme A reductase reporter construct occurs in the endoplasmic reticulum" (1994) *J. Cell Sci.* 107(Pt.9):2635–2642.

Lewis, et al. "Crystal Structure of the Lactose Operon Repressor and Its Complexes with DNA and Inducer" (1996) *Science* 271:1247–1254.

Li, X. and Greenwald, I. "Additional evidence for an eight–transmembrane–domain topology for *Caenorhabditis elegans* and human presenilins" (1998) *Proc. Natl. Acad. Sci. USA* 95:7109–7114.

Miyamoto, et al. "Differential Modes of Nuclear Localization Signal (NLS) Recognition by Three Distinct Classes of NLS Receptors" (1997) *J. Biol. Chem.* 272:26375–26381.

Podlisny et al. "Presenilin Proteins Undergo heterogeneous Endoproteolysis between Thr$_{291}$ and Ala$_{299}$ and Occur as Stable N–and C–Terminal Fragments in Normal and Alzheimer Brain Tissue" (1997) *Neurobiol. Dis.*3:325–337.

(List continued on next page.)

*Primary Examiner*—Ponnathapu Achutamurthy
*Assistant Examiner*—Christian L. Fronda
(74) *Attorney, Agent, or Firm*—Greenlee Winner and Sullican PC

(57) ABSTRACT

The present disclosure provides DNA constructs, genetically modified host cells and methods for identifying inhibitors of proteolysis of membrane-associated protease substrates including, but not limited to, amyloid precursor protein, a Notch protein and sterol response element binding proteins. The methods rely on chimeric proteolytic substrates containing a portion of the proteolytic substrate protein (including the proteolytic cleavage site) and a transcription repressor protein portion. Release of the repressor results in blockage of the transcription of a chimeric reporter gene which includes repressor-responsive transcription regulatory sequences and a reporter protein coding region. A specific protease inhibitor is identified by increased reporter protein activity.

48 Claims, 12 Drawing Sheets

OTHER PUBLICATIONS

Rawson, et al. "Complementation Cloning of S2P, a Gene Encoding a Putative Metalloprotease Required for Intramembrane Cleavage of SREBPs" (1997) *Molecular Cell* 1:47–57.

Sakai, et al. "Molelcular Identification of the Sterol–Regulated Luminal Protease that Cleaves SREBPs and Controls Lipid Composition of Animal Cells" (1998) *Molecular Cell* 2:505–514.

Sakai et al. "Sterol–Regulated Release of SREBP–2 from cell Membranes Requires Two Sequential Cleavages, One Within a Transmembrane Segment" (1996) *Cell* 85:1037–1046.

Sakai, et al. "Cleavage of Sterol Regulatory Element–binding Proteins (SREBPs) at Site–1 Requires Interaction with SREBP Cleavage–activating Protein" (1998) *J. Biol. Chem.* 273:5785–5793.

Selkoe, D.J. "Amyloid β–Protein and the Genetics of Alzheimer's Disease" (1996) *J. Biol. Chem.* 271:18295–18298.

Selkoe, D.J. "Alzheimer's Disease: Genotypes, Phenotype, and Treatments" (1997) *Science* 275:630–631.

Shaw, G. "The pleckstrin homology domain: an intriguing multifunctionl protein module" (1996) *BioAssays* 18(1):35–46.

Shimomura, et al. "Insulin resistance and diabetes mellitus in transgenic mice expressing nuclear SREBP–1c in adipose tissue: model for congenital generalized lipodystrophy" (1998) *Genes Devel.* 12:3182–3194.

Simon, S. "Translocation of proteins across the endoplasmic reticulum" (1993) *Curr. Opin. Cell. Biol.* 5:581–588.

Struhl, G. and Adachi, A. "Nuclear Access and Action of Notch In Vivo" (1998) *Cell* 93:649–660.

Szczesna–Skorupa et al. "Mobility of cytochrome P450 in the endoplasmic reticulum membrane" (1998) *PNAS* 95:14793–14798.

Thinakaran, et al. "Endoproteolysis of Presenilin 1 and Accumulation of Processed Derivatives In Vivo" (1996) *Neuron* 17:181–190.

Tomita et al. "βAPP γ–secretase and SREBP site 2 protease are two different enzymes" (1998) *NeuroReport* 9:911–913.

Wang, et al. "SREBP–1, a Membrane–Bound Transcription Factor Released by Sterol–Regulated Proteolysis" (1994) *Cell* 77:53–62.

Wolfe, et al. "A Substrate–Based Difluoro Ketone Selectively Inhibits Alzheimer's γ–Secretase Activity" (1998) *J. Med. Chem.* 41:6–9.

* cited by examiner

Reporter (pRSVO-luc)

LacI control (pCMV-LacI)

Fusion substrates (pCMV-APPI & pCMV-ISRP)

METHODS AND REAGENTS FOR IDENTIFYING INHIBITORS OF PROTEOLYSIS OF MEMBRANE-ASSOCIATED PROTEINS

CROSS REFERENCE TO RELATED APPLICATIONS not applicable

ACKNOWLEDGEMENT OF FEDERAL RESEARCH SUPPORT not applicable

BACKGROUND OF THE INVENTION

The present invention relates to methods and reagents for identifying compounds which inhibit proteolysis of polypeptides, especially membrane-associated polypeptides.

The amyloid precursor protein (APP) is an integral membrane protein located predominantly within intracellular vesicles. One of the well-characterized proteolytic processing pathways of APP results in the generation of a 40 or 42 amino acid peptide (Aβ40–42). Extracellular deposition and plaque formation nucleated by these amyloid Aβ peptides form a hallmark lesion in the brains of Alzheimer's disease patients [Selkoe, D. J. (1996) J. Biol. Chem. 271:18295–18298]. Aβ40–42 peptides are generated from the specific and sequential cleavage of the membrane-bound APP by the β and γ-secretases [Selkoe, D. J. (1997) Science 275:630–631; Lamb, B. T. (1997) Nature Med. 3:28–29]. β-secretase cleaves on the lumenal side of the ER and, together with the subsequent intrinsic membrane cleavage by γ-secretase, determines the rate of Aβ40–42 generation. Notably, the γ-secretase cleavage of APP bears a striking similarity to that of the SREBP S2P cleavage and, except for Notch processing (discussed below), is the only other known example of specific proteolysis occurring within a membrane-spanning segment [Brown and Goldstein (1997) Cell 89:331–340; Sakai et al. (1996) Cell 85:1037–1046]. Recently, the APP γ-secretase and SREBP S2P have been shown to be two distinct enzymes [Tomita et al. (1998) NeuroReport 9:911–913].

The Notch receptor family includes Notch in Drosophila, LIN-12 and GLP-1 in C. elegans, and mNotch1 and mNotch2 in mouse, among others [Artavanis-Tsakonas et al. (1995) Science 268:225–232]. During development, Notch mediates cell-cell communications required for a variety of cell fate decisions and for axon guidance. Notch family members are large, multidomain proteins that consist of a single transmembrane domain and large extracellular and intracellular domains. Proteolytic cleavage of Notch is believed to result in release of the intracellular domain, which translocates to the nucleus and associates with a DNA-binding subunit [Li, X, and Greenwald, I. (1998) Proc. Natl. Acad. Sci. USA 95:7109–7114; Thinakaran et al. (1996) Neuron 17:181–190; Podlisny et al. (1997) Neurobiol. Dis. 3:325–337; Capell et al. (1998) J. Biol. Chem. 273:3205–3211]. A processing step responsible for releasing the intracellular domain takes place in or near the transmembrane domain [Li and Greenwald (1998) supra]. Thus, Notch appears to undergo proteolytic events that resemble those involved in cleavage of APP, i.e., sequential hydrolysis by β and γ-secretases.

The regulation of hepatic cholesterol biosynthesis is central to the understanding of hypercholesterolemia as a risk factor for cardiovascular disease [Goldstein and Brown (1997) Nature 343:425–430]. A sterol-activated transcription factor, the sterol regulatory element binding protein (SREBP), specifically binds sterol regulatory elements (SREs) in the regulatory region of a number of coordinately regulated genes, including the promoters of the low density lipoprotein (LDL) receptor and 3-hydroxy-3-methylglutaryl coenzyme A (HMG-CoA) reductase [Briggs et al. (1993) Cell. 77:53–62; Wang et al. (1993) J. Biol. Chem. 268:14497–14504]. SREBP is maintained in an inactive state by its targeted localization to the endoplasmic reticulum (ER) membrane. Upon cholesterol deprivation, the amino-terminal portion of SREBP is specifically proteolyzed and liberated from its ER anchor in a two-step process [Wang et al. (1994) J. Biol. Chem. 271:10379–10384; Hua et al. (1996) J. Biol. Chem. 271:10379–10384; Sakai et al. (1996) supra]. This cleavage releases the amino-terminal segment of SREBP, allowing it to enter the nucleus, where it binds to enhancers and activates transcription of genes encoding the LDL receptor and multiple enzymes of cholesterol and fatty acid biosynthesis [Brown and Goldstein (1997) supra]. Sterols regulate initial proteolysis at site 1, which appears to be a prerequisite for site 2 hydrolysis, which occurs within the ER bilayer. The cDNA encoding the protease responsible for site 2 cleavage of the SREBPs (site 2 protease (S2P)) was isolated by complementation cloning and encodes a putative zinc metalloprotease with multiple transmembrane domains [Rawson et al. (1997) Mol. Cell. 1:47–57]. The site 1 protease (S1P), a membrane-bound subtilisin-related serine protease, has also recently been cloned and characterized [Espenshade et al. (1999) J. Biol. Chem. 274:22795–22804].

Due to the importance of membrane-associated proteolysis in gene expression, cellular differentiation and disease, considerable research effort has focused on membrane proteins, and particularly on identifying enzymes involved in their proteolytic pathways. Despite these efforts, until recently, only one of the several inferred proteolytic enzymes responsible for APP, SREBP and Notch maturation had been identified. Although at least three such proteases have now been cloned, specific and nontoxic inhibitors of these enzymes are not yet available. Thus, a need exists for an accurate, sensitive and economical high throughput screen to identify novel nontoxic inhibitors of proteolysis, especially membrane-associated proteolysis. In addition, due to the difficulty in isolating enzymes involved in lumenal and intrinsic membrane proteolysis, there exists a need for a simple and reliable technique which will enable tho large-scale screening of compounds for antiproteolytic activity without the need to first clone the target protease. The present invention fulfills these and other needs.

SUMMARY OF THE INVENTION

The present invention provides methods and compositions for identifying compounds which inhibit proteolysis of cellular proteins, particularly intrinsic membrane proteins and membrane-associated proteins. More specifically, the invention relates to methods and compositions for identifying compounds which prevent the functional interaction between a protease and its corresponding recognition site on a proteolytic substrate. Compounds that disrupt or prevent the functional interaction between these two proteins have significant modulatory effects on receptor maturation and signal transduction, and thus are useful for treating and/or preventing a wide variety of diseases and pathological conditions associated with transmembrane proteolytic events. Such conditions include, for example, neurological disorders, cardiac diseases, and metabolic diseases. Many of these compounds have potent neuroprotective properties which prove especially usefull for the prevention and/or treatment of neurodegenerative disorders such as Alzheimer's disease, as well as for the prevention and/or treatment of cardiovascular diseases and diabetes.

In one aspect, the invention provides methods of evaluating and screening candidate compounds for the ability to inhibit proteolysis of a proteolytic substrate. The methods comprise preparing a genetically modified (recombinant) host cell which expresses (i) a chimeric polypeptide comprising a transcription repressor and a protease recognition site, wherein the chimeric polypeptide is desirably attached to a non-nuclear membrane, and (ii) a reporter gene operably linked to transcription regulatory sequences which are responsive to the transcription repressor and which include a promoter. The candidate compound is then added to the modified host cell, and expression of the reporter gene is monitored. An increase in reporter gene expression over expression in the absence of the test compound is an indication that the compound inhibits proteolysis of the proteolytic substrate.

Reporter genes desirably give rise to gene products which can be quantitated, either in terms of amount of protein synthesized or in terms of enzymatic or luminescence activity. Suitable reporter proteins can include firefly or bacterial luciferase, β-glucuronidase, β-galactosidase, green fluorescent protein, red fluorescent protein, aequorin, chloramphenicol acetyl transferase, alkaline phosphatase, horseradish peroxidase, among others. Suitable transcription regulatory elements include those with negative regulation (i.e., downstream gene expression is blocked by the binding of a repressor protein or polypeptide to the corresponding transcription control sequences).

In another aspect, the invention provides genetically modified host cells and methods for evaluating or screening candidate compounds for antiproteolytic activity. The modified host cells contain a hybrid (chimeric or fusion) protein comprising a protease recognition site and a transcription repressor portion and a membrane targeting portion, wherein the first hybrid protein is attached to a non-nuclear membrane (e.g., the endoplasmic reticulum), and a chimeric reporter gene comprising a reporter enzyme or protein coding sequence operably linked to a repressible promoter. The modified host cell may optionally comprise a nuclear localization signal in polypeptide linkage to the protease recognition site and/or the transcription repressor in the first hybrid protein. Proteolytic cleavage of the fusion protein releases the repressor portion of the fusion protein, which can then bind to the operator sequences associated with the chimeric reporter gene to prevent transcription. A test compound is identified as a protease inhibitor when incubation of the recombinant host cell in the presence of the test compound results in a detectable increase in expression of the reporter (due to absence of a soluble, active repressor in the recombinant cell).

In other aspects, the invention provides polynucleotides, expression vectors, and host cells transfected or transformed with expression vectors containing nucleotide sequences which encode a transcription repressor, a nuclear localization signal, and a protease recognition site of a proteolytic substrate. In preferred embodiments, the proteolytic substrate is an amyloid precursor protein (APP), a sterol regulatory element binding protein (SREBP), or a Notch receptor protein.

As specifically exemplified herein, CHO-K1 cells are the recombinant host cells in which the assay is carried out, the reporter gene is the luciferase coding sequence coupled to the lac operator, and the chimeric protein includes the lac repressor protein, an endoplasmic reticulum-binding region and a protease recognition site from either the amyloid precursor protein, the sterol response element binding protein or the Notch protein. Cleavage of the chimeric protein by a cellular protease releases the lac repressor, which prevents reporter gene expression. The chimeric protein can further comprise a nuclear localization signal linked to the repressor portion so that proteolysis of the chimeric protein results in nuclear localization of the repressor. In the absence of an inhibitor of the proteolytic event, the reporter gene is substantially silent due to repressor release and binding to the operator region upstream of the reporter protein's coding sequence. Where an inhibitor of the proteolysis is present, there is a reduced amount of repressor released (or none), and the result is a detectable increase in the level of reporter gene product.

vector or lacI-containing fusion plasmids. Cells were maintained for 36–48 hrs post-transfection in medium supplemented with 10% lipoprotein-deficient serum in the absence (−) or presence (+) of sterols (10 μg/ml of cholesterol, 1 μg/ml of 25-hydroxycholesterol). Altered templates are designated S1 and S2 for the site 1 and site 2 SREBP mutants respectively. The data represent the mean ±SEM of triplicate experiments.

Figure 7:
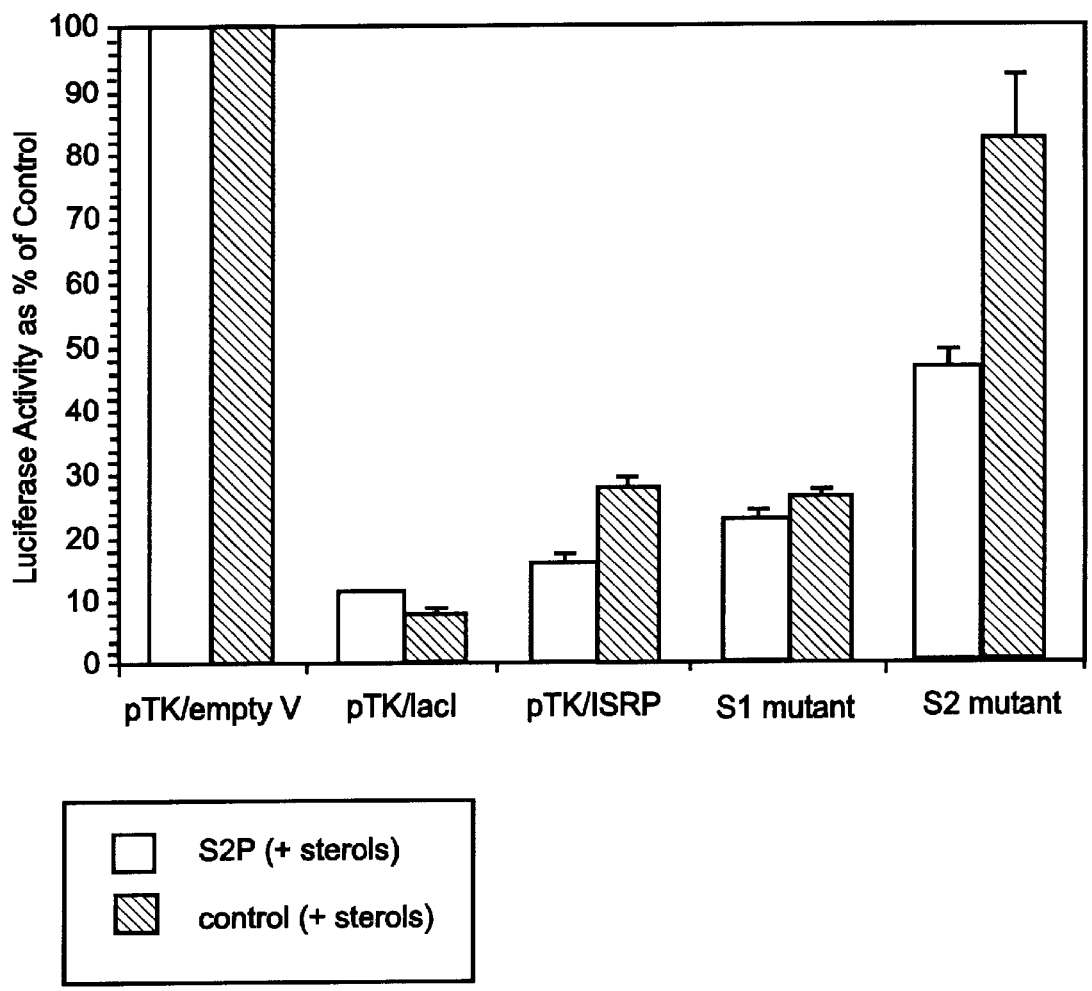

FIG. 7 illustrates that over-expression of S2P can partially override the sterol depletion and protease cleavage (target) site sequence requirements. Transient transfections were performed in the presence of sterols. The pRSVO-luc reporter and either empty vector of pCMV-S2P (site 2 protease) were cotransfected with of the lacI-containing fusions.

Figure 8:
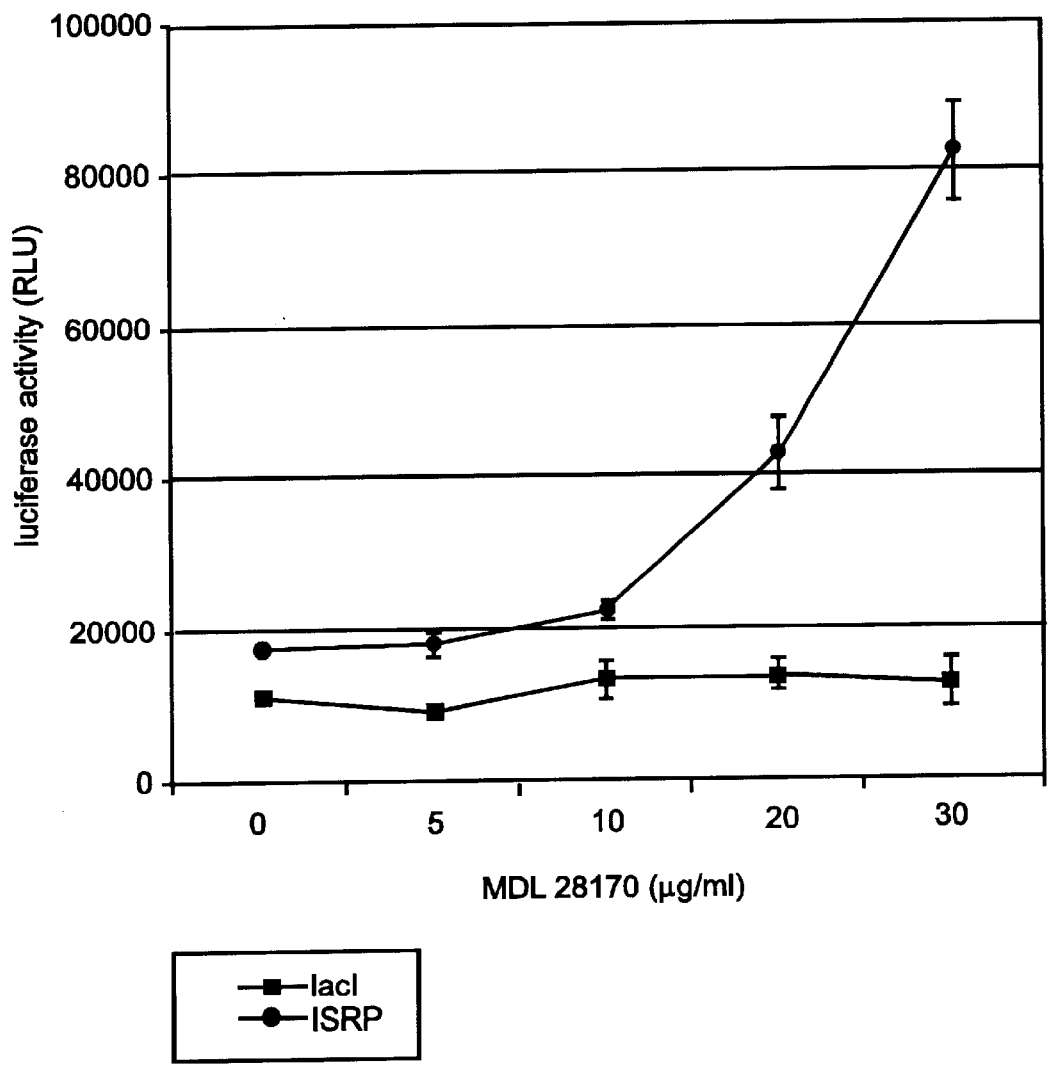

FIG. 8 demonstrates a pharmacological block of SREBP processing. CHO-K1 cells were transfected with pRSVO-luc and either pCMV-LacI or pCMV-ISRP. The small molecule MDL 28170 was applied for 36–48 hrs at the concentrations shown.

Figure 9:
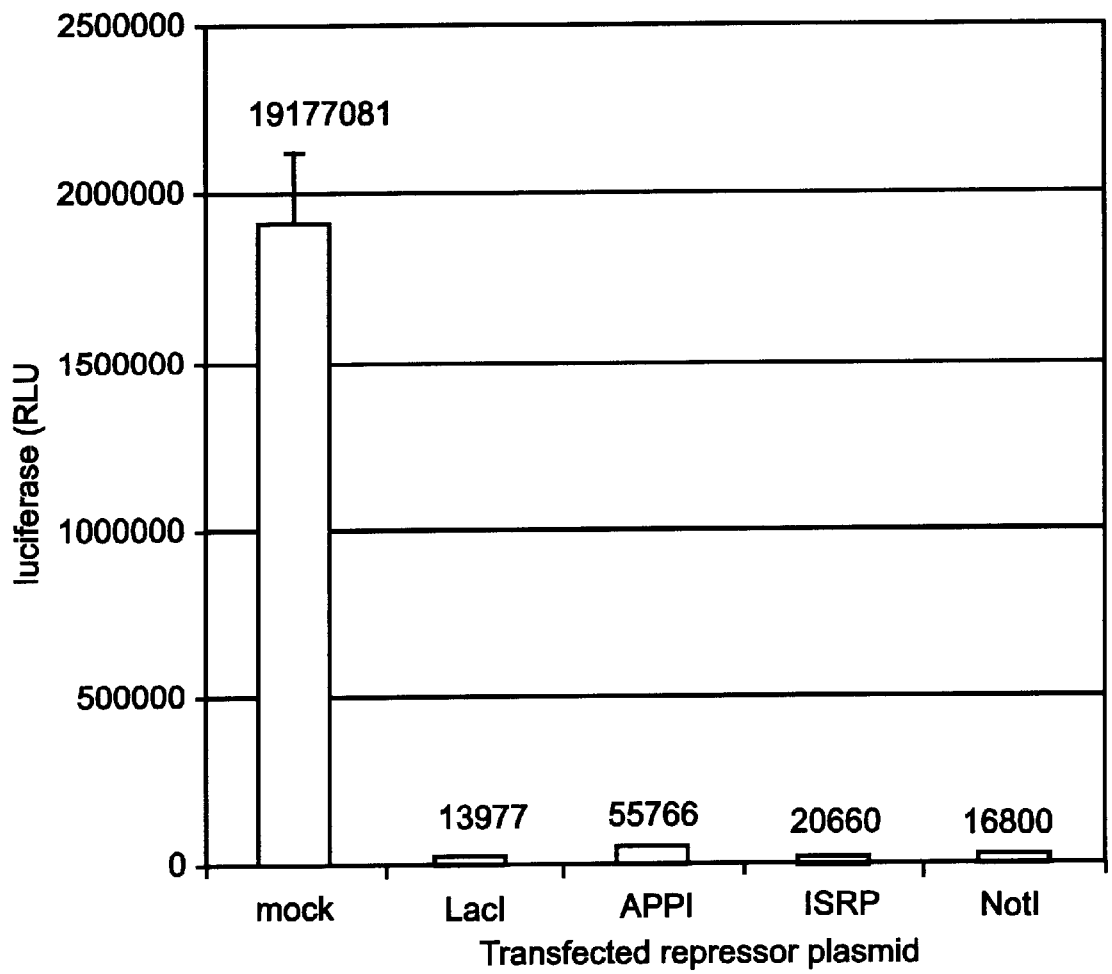

FIG. 9 shows reporter gene repression by a co-transfected lacI fusion construct. CHO-K1 cells were transfected with pRSVO-luc and various repressor fusion constructs. Cells that received a repressor construct exhibit marked decreases in luciferase activity when compared to the mock control.

Figure 10A:
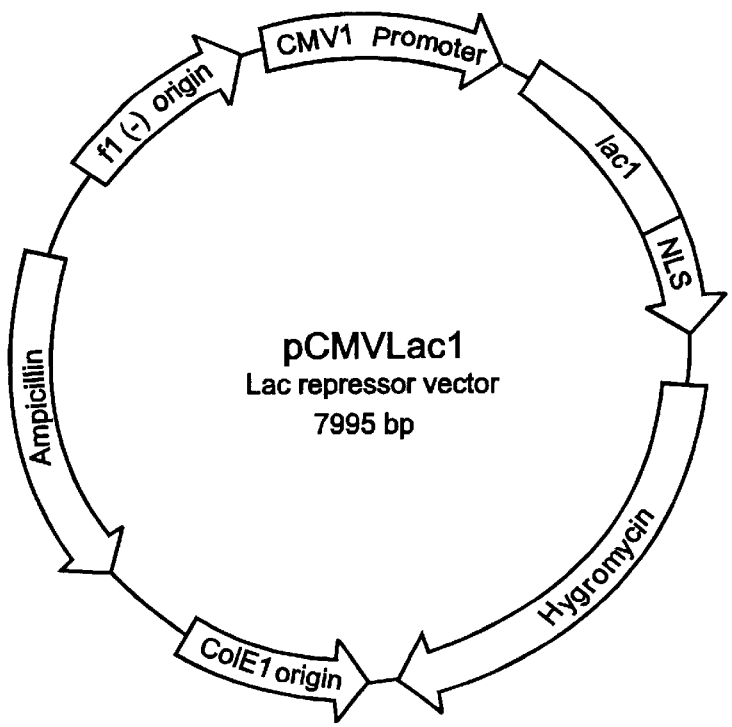
Figure 10B:
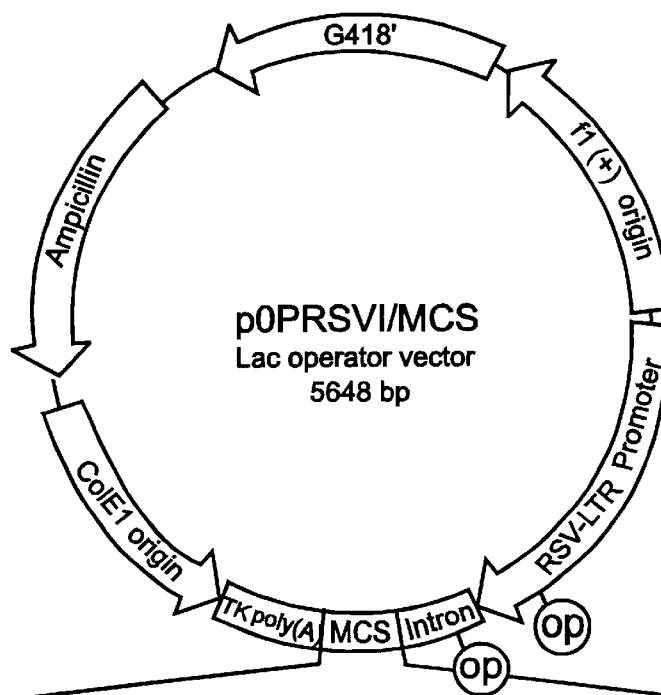
Figure 10C:
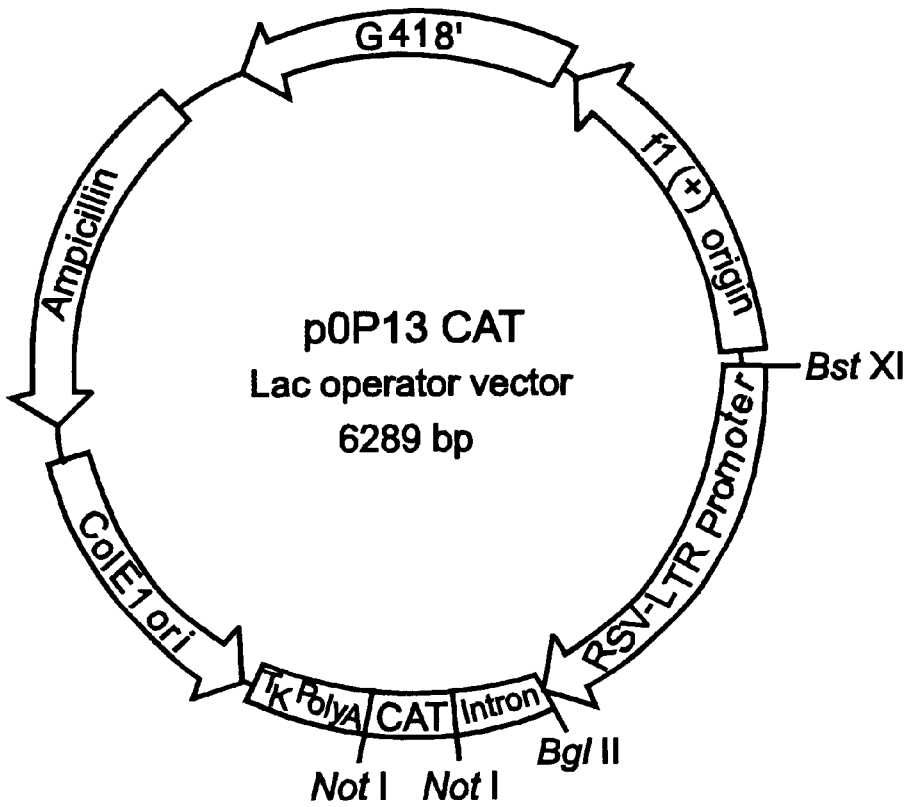
Figure 10D:
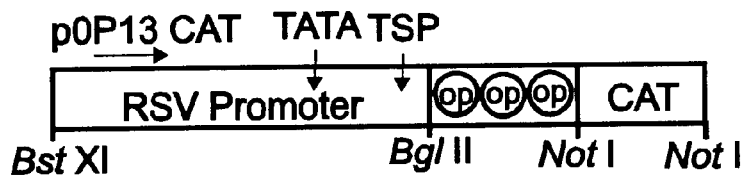

FIGS. 10A–10D show the vectors (purchased from Stratagene, La Jolla, Calif.) used in the present invention. FIG. 10A is a diagram of pCMVLacI, which contains a lacI-NLC coding sequence. FIG. 10B illustrates pOPRSVI/MCS, which contains the RSV-LTR promoter, two lac operator sequences and a multiple cloning site. FIG. 10C shows the structure of pOP13CAT, which contains the RSV-LTR promoter, three lac operators and a CAT reporter gene. FIG. 10D provides further detail of the promoter-operator-reporter gene region of pOP13CAT.

BRIEF DESCRIPTION OF THE SEQUENCES

SEQ ID NO:1 APP-LacI fusion protein coding sequence on a HindIII-XbaI fragment of pCMV-APPI.

SEQ ID NO:2 Amino acid sequence of the APP-LacI fuision protein

SEQ ID NO:3 Notch-LacI fusion protein coding sequence on a HindIII-XbaI fragment of pCMV-NotI SEQ ID NO:4 Amino acid sequence of the Notch-LacI fuision protein SEQ ID NO:5 KpnI-XhoI restriction fragment comprising ISRP coding sequence SEQ ID NO:6 Amino acid sequence encoded on KpnI-XhoI fragment of pCMV-ISRP SEQ ID NO:7 Nuclear localization sequence from SV40 large T antigen SEQ ID NO:8 P450 transmembrane domain coding sequence on a HindIII-BspEI fragment SEQ ID NO:9 Amino acid sequence of P450 transmembrane domain SEQ ID NO:10 Caspase-3/linker coding sequence SEQ ID NO:11 Caspase-3/linker amino acid sequence SEQ ID NO:12–13 Oligonucleotide primers for amplifying APP coding fragment SEQ ID NO:14–15 Oligonucleotide primers for amplifying LacI-NLS coding fragment SEQ ID NO:16–17 Oligonucleotide primers for amplifing SREBP-2 coding fragment SEQ ID NO:18–19 Oligonucleotide primers for amplifying LacI-NLS coding fragment SEQ ID NO:20–21 Oligonucleotide primers for amplifying mouse Notch TM domain coding fragment SEQ ID NO:22–23 Oligonucleotide primers for amplifying rat Notch TM domain coding fragment SEQ ID NO:24–25 Oligonucleotide primers for PCR cloning of pTMI SEQ ID NO:26 Sequence coding for caspase-3 and peptide linker fragment SEQ ID NO:27 Sequence of caspase-3 cleavage sites and peptide linkers SEQ ID NO:28–29 Oligonucleotide primers in PCR cloning of pTMI-C3

SEQ ID NO:30 Site-1 protease recognition sequence in SREBP-2

SEQ ID NO:31 Site-1 protease recognition sequence in hamster and human SREBP-2

SEQ ID NO:32 Site-2 protease recognition sequence in SREBP-2

DETAILED DESCRIPTION OF THE INVENTION

Unless defined otherwise, all technical and scientgic terms used herein have the same meaning as commonly understood by one of ordinary skill in the art to which this invention pertains. Although any methods and materials similar or equivalent to those described herein can be used in the practice or testing of the present invention, the preferred methods and materials are described. For purposes of the present invention, the following terms are defined below.

As used herein, the term chimeric is used to signify that the portions of an expressible coding sequence or protein originate from different sources. For example, the components of a fusion protein are derived from diverse proteins or a chimeric reporter gene contains transcription regulatory sequences which are of a different organism or gene source than the coding portion.

In the context of the present application, a non-nuclear membrane is any membrane within a eukaryotic cell except the membrane enclosing the nucleus.

As used herein, the term biologically active fragment means a portion of an repressor region capable of binding to cognate operator region (transcriptional regulatory sequence on a DNA molecule, especially that linked to a reporter coding sequence). The term fragment, as applied in this context, will typically be at least about 6 amino acids, usually at least about 8 contiguous amino acids, preferably at least about 10 contiguous amino acids, more preferably at least about 12 contiguous amino acids, and most preferably at least about 14 or more contiguous amino acids in length. Such fragments can be generated by methods known to those skilled in the art, including proteolytic cleavage of the polypeptide, de novo synthesis of the fragment, or through genetic engineering for recombinant expression.

Figure 1A:
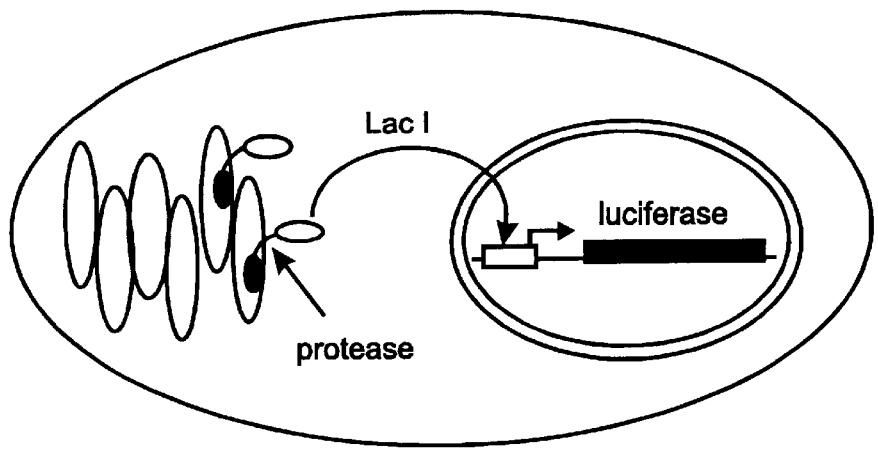
FIG. 1A diagrammatically illustrates the repressor release assay. A protease substrate-lacI fusion is expressed and localizes to the endoplasmic reticulum. Resident cellular processing proteases release the lacI repressor from its ER tether, allowing it to relocalize to the nucleus where it represses reporter gene transcription.
Figure 1B:
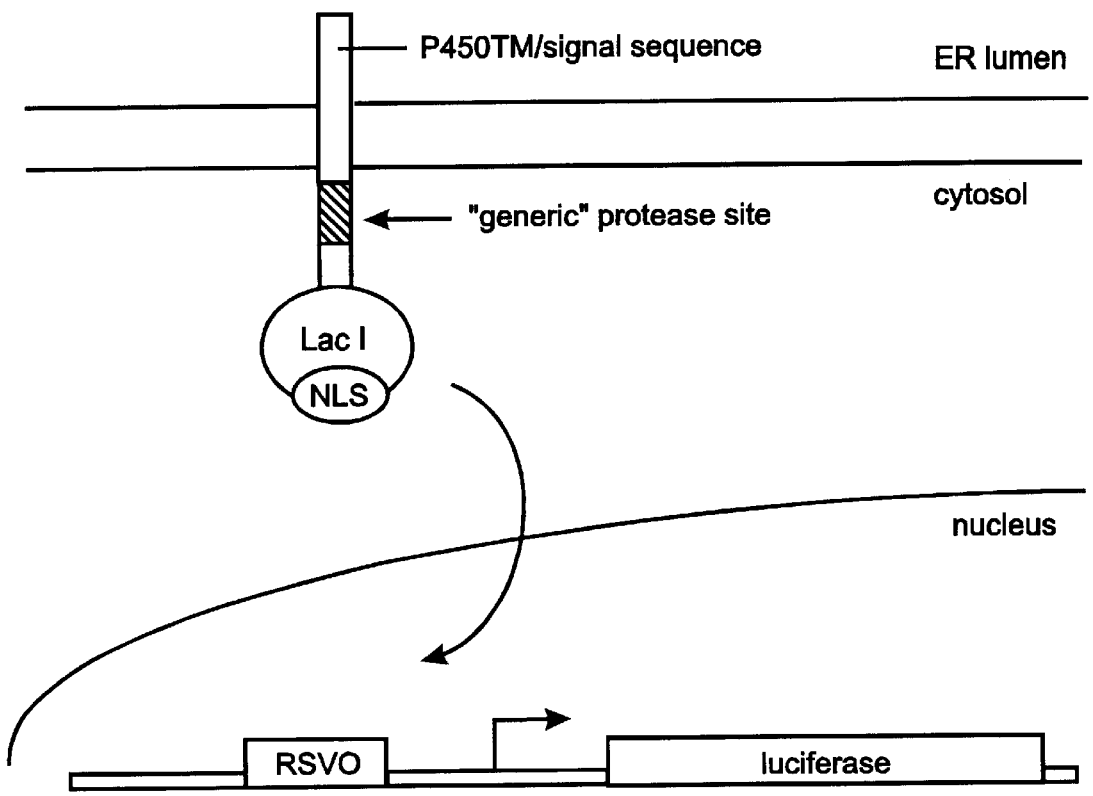
FIG. 1B diagrammatically illustrates the repressor release assay as carried out with a membrane-associated fusion protein having the P450 transmembrane and a lacI repressor portion with a lac-regulated luciferase reporter gene.

A cell compartment localization domain can be a plasma membrane localizing domain such as the sequence of v-Src that acts as a myristoylation signal, the sequence of H-Ras that acts as a signal for farnesylation and palmitoylation, or the sequence of K-Ras4B that acts a farnesylation signal. Expression of a fusion protein containing one of these domains results in farnesylation or myristoylation of the fusion protein and localization of the fusion protein or a complex containing the fusion protein to the plasma membrane. In addition, a domain such as a pleckstrin homology domain can be usefull for localizing a fusion protein to the plasma membrane. For a description of plasma membrane localizing domains useful in the present invention, see, for example, Buss et al. (1988) *Mol. Cell. Biol.* 8:3960–3963; Karin et al., U.S. Pat. No. 5,776,689; Hancock et al. (1991) *EMBO J.* 10:4033–4039; and Shaw (1996) BioEssays 18:35–46, each of which is incorporated by reference in its entirety herein. See also Broder et al. (1998) *Curr. Biol.* 8(20):1121–1124, and Aronheim et al. (1997) *Mol. Cell. Biol.* 17(6):3094–3102, both of which are incorporated by reference herein. Proteins can be targeted to the endoplasmic reticulum via a particular targeting sequence such as that specifically exemplified by the transmembrane domain/signal sequence of P450 (See also FIG. 1B and SEQ ID NOs:8 and 9). Alternatively, the transmembrane domain of a Notch protein can serve this function.

As used herein, a nuclear localization signal (or sequence) (NLS) is a region of a polypeptide which targets the polypeptide to the nucleus of the cell. One such NLS is that from the SV40 large T antigen. See, e.g., U.S. Pat. No. 5,589,392 [Short (1996), incorporated herein by references; Kalderon et al. (1984) *Cell* 39:499–509]. The minimum region of the SV40 large T antigen with NLS activity is Pro-Lys-Lys-Lys-Arg-Lys-Val (SEQ ID NO:7). See also U.S. Pat. No. 5,776,689, Karin et al.

As used in the present application, a fusion protein is a protein that contains at least two polypeptide regions and a linking peptide to operatively link the two polypeptides into one continuous polypeptide. The two polypeptide regions linked in a fusion protein are derived from different sources, and therefore a fusion protein comprises two linked polypeptide regions not normally joined together in nature.

As used herein, a linking sequence (or linker peptide) contains one to seven amino acid residues joined in peptide bonds. A linking sequence serves to join two polypeptide regions of differing origins via a peptide bond between the linking sequence and each of the polypeptide regions.

Typically, a fusion (or chimeric or hybrid) protein is synthesized as a continuous polypeptide in a recombinant host cell which contains an expression hybrid (chimeric) coding sequence in which the polypeptide regions' coding sequence regions are fised in frame on either side of the linker peptide's coding sequence. The chimeric coding sequence (encoding the fusion protein) is operatively linked to expression control sequences functional in a recombinant host cell of choice.

As used herein, a protease recognition region (sequence or portion) refers to a portion within a protein which includes an amino acid sequence which is required for proteolytic cleavage by a protease of interest, and also desirably, it is derived from the amino acid sequence of a protease substrate protein of interest, including but not limited to, the amyloid precursor protein, the sterol response element binding protein and the Notch protein. In the present context, a protease recognition sequence is recognized by a membrane-associated or a soluble protease, and it is desirably located with a fuision protein between a transcription repressor region and a membrane localization (or targeting) region.

As used herein, a proteolytic cleavage site is the site where the amide linkage between amino acid residues within a protease substrate protein is actually broken. A protease substrate protein is one which is cleaved by a particular protease. The repressor release assay methods of the present invention utilize chimeric, membrane-associated protease substrate proteins.

The amino acid sequence within the SREBP-2 protein which includes the S1P protease recognition region, on the lumenal side of the ER membrane, is Pro-His-Ser-Gly-Ser-Gly-Arg-Ser-Val-Leu-Ser-Phe-Glu (SEQ ID NO:30) [Sakai et al. (1998) *Molecular Cell.* 2:505–514]. The protease cleaves the bond between the tenth and eleventh amino acid residues of this sequence. The Site-1 protease (S1P) requires an Arg three residues on the N-terminal site of the cleaved Leu-Ser bond. In hamster and human SREBP-2, the sequence is Arg-Ser-Val-Leu-Ser (SEQ ID NO:31). Even though it cuts on the lumenal side of the membrane, the Site-1 protease requires the C-terminal domain of SREBP-2. The Site-2 enzyme (S2P) requires the sequence Asp-Arg-Ser-Arg (SEQ ID NO:32) which is immediately external (cytosolic) to the first transmembrane domain of SREBP-2. Proteolytic cleavage by S2P occurs within the transmembrane domain.

In one embodiment, the method comprises adding a candidate compound to a recombinant host cell comprising the hybrid repressor gene and the chimeric reporter gene and comparing the level of expression of a reporter protein in the presence and absence of the candidate compound, wherein the recombinant host cell exhibits an increase in reporter activity when the candidate compound inhibits proteolysis of the chimeric repressor protein.

As used herein, with regard to a protein, the terms domains, regions and portions are synonymous.

In another aspect, the invention provides recombinant host cells which are useful for screening candidate compounds for protease-inhibiting activity, especially activity inhibiting a membrane-associated protease. In a preferred embodiment, the modified host cell comprises a hybrid protein comprising a DNA-binding domain of a repressor protein in polypeptide linkage to a protease cleavage site, and desirably to a membrane targeting region (where membrane-associated protease inhibitors are sought). The chimeric repressor protein can, optionally, further include a nuclear localization domain. The recombinant host cells of the present invention further contain heterologous DNA encoding a chimeric reporter gene comprising transcription regulatory sequences including the operator sequence to which the repressor binds specifically and a coding sequence encoding a reporter protein, the coding sequence being operably linked to the transcription regulatory sequence such that the reporter is synthesized when the repressor protein is not bound to the operator region of the transcription regulatory sequences.

Briefly, in the present method, a candidate compound is introduced into the system (the recombinant host cell), and a change in a reporter or marker protein product is assayed. Any compoumd which alters the level of expression of the reporter or marker, as monitored by a suitable assay, is a potential drug candidate and may be suitable for further, in-depth studies of therapeutic applications. The candidate compound may be of any form suitable for entry into the cytoplasm and/or nucleus of the recombinant host cell. Under appropriate conditions, the candidate compound may be allowed to freely diffluse into the cell, or the delivery of the compound may be facilitated by techniques and substances which enhance cell permeability, a wide variety of which are known in the art. Methods for increasing cell permeability include, without limitation, the use of organic solvents such as dimethylsulfoxide, hydrolytic enzymes (which degrade cell walls), yeast cell mutants (e.g., erg-), liposomes, application of electrical current, and physical means such as compound-coated teflon pellets.

The host organism (recombinant host cell) may be any eukaryotic or prokaryotic cell, or multicellular organism.

Suitable host cells include mammalian cells, such as Chinese hamster ovary cells (CHO), the monkey COS-1 cell line, and the mammalian cell CV-1, or amphibian cells, such as Xenopus egg cell, or yeast cells or insect cells can be used for the testing methods. Additionally, where desired, insect cells may be utilized as host cells in the method of the present invention. See, e.g. Miller et al. [*Genetic Engineering* (1986) 8:277–298, Plenum Press] and references cited therein. In preferred embodiments, the recombinant host cell is a mammalian cell, especially a CHO-K1 cell. The recombinant host cell can also include yeast cells selected from the group consisting of *Saccharomyces cerevisiae, Schizosaccharomyces pombe*, and *Pichia pastoris*, Various strains of *E. coli* (e.g., HB101, MC1061) are well-known as host cells, in particular for molecular biological manipulations. Various strains of *B. subtilis*, Pseudomonas, other bacilli and the like may also be employed.

The invention includes polynucleotides, expression vectors, and recombinant host cells transfected or transformed with expression vectors containing nucleotide sequences which encode a chimeric protein comprising a transcriptional repressor portion or active fragment thereof and a portion having a proteolytic cleavage site; desirably the chimeric protein further comprises a membrane targeting domain (e.g., an ER-targeting domain). The chimeric protein is such that there is no repression of the transcription of the reporter gene unless the cognate protease has acted upon the cleavage site to release the transcriptional repressor portion which can then interact with the transcriptional regulatory sequences associated with the chimeric reporter gene to repress (prevent) expression.

The similarities of the APP and SREBP proteolytic pathways have been reviewed [Brown and Goldstein (1997) supra]. Similar features include the membrane embedded substrate topologies, accessory proteins and sequential cleavage sites. To date, only one of the four inferred proteases responsible for APP and SREBP maturation has been identified. Therefore, the present inventors chose to bypass the cloning of the protease(s) and instead to exploit endogenous cellular proteolytic activities to develop an easy and sensitive assay for these membrane associate proteolytic events. Recombinant lacI-APP and lacI-SREBP substrates were engineered and targeted to the membranes of the ER. After specific proteolysis, the lac repressor segregated to the nucleus via the incorporated NLS [Miyamoto et al. (1997) *J. Biol. Chem.* 272:26375–26381; U.S. Pat. No. 5,776,689]. In the nucleus, the released repressor bound to the lac operator sequences upstream of the reporter coding sequence to repress transcription. See FIG. 1A.

Figure 2A:
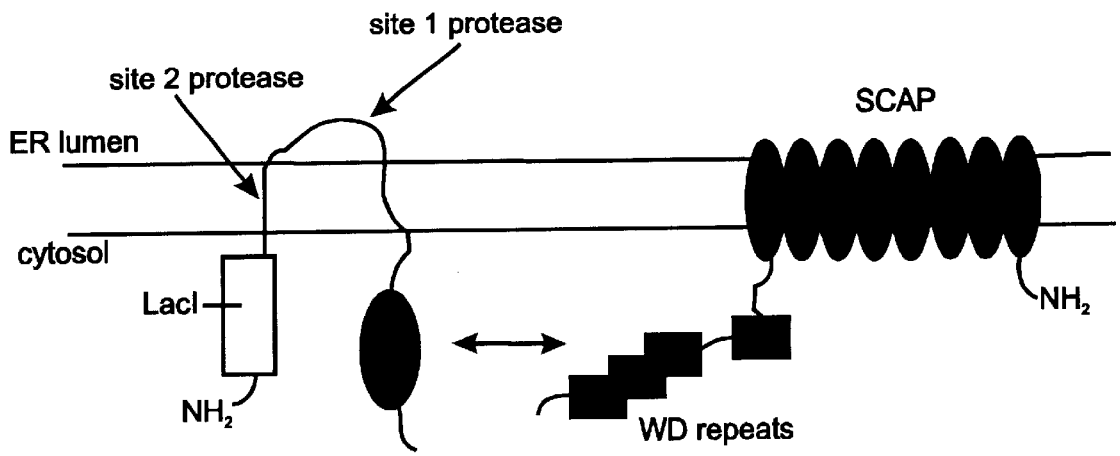
FIG. 2A shows membrane topology and proteolytic sites schematic of the SREBP-lacI fusion substrate.
Figure 2B:
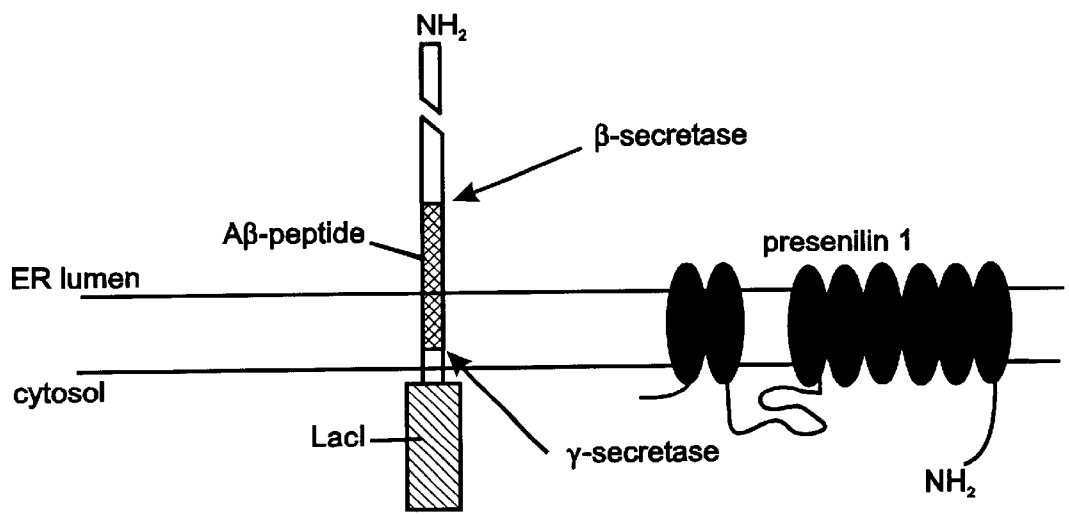
FIG. 2B diagrammatically illustrates membrane topology, proteolytic recognition sites and accessory protein schematic of the APP-lacI fission substrate. APP1, fusion substrate; presenilin, influences secretase activity.
Figure 2C:
FIG. 2C presents diagrams of plasmid constructs used in experiments described hereinbelow. Shown are the lacI-responsive reporter (pRSVO-luc), the control lacI expression plasmid (pCMV-lacI), and the protease substrate-lacI fusion expression constructs (pCMV-APPI and pCMV-ISRP).
Figure 2C:
Figure 2C:
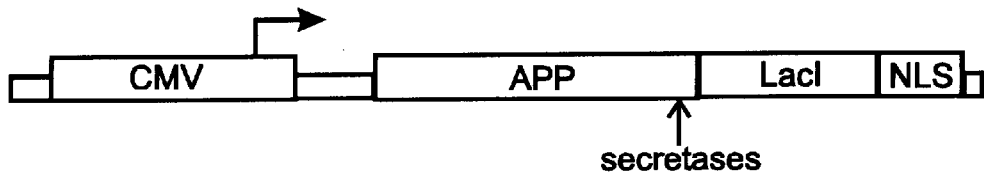
Figure 2C:
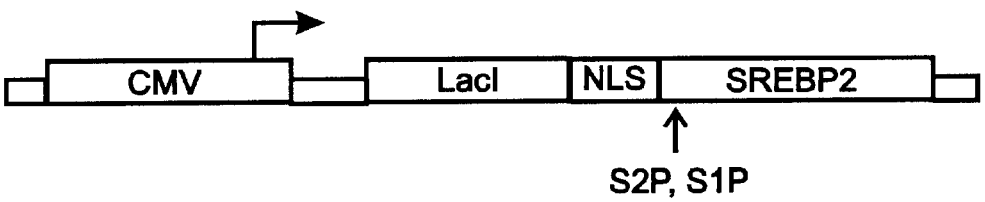
Figure 4:
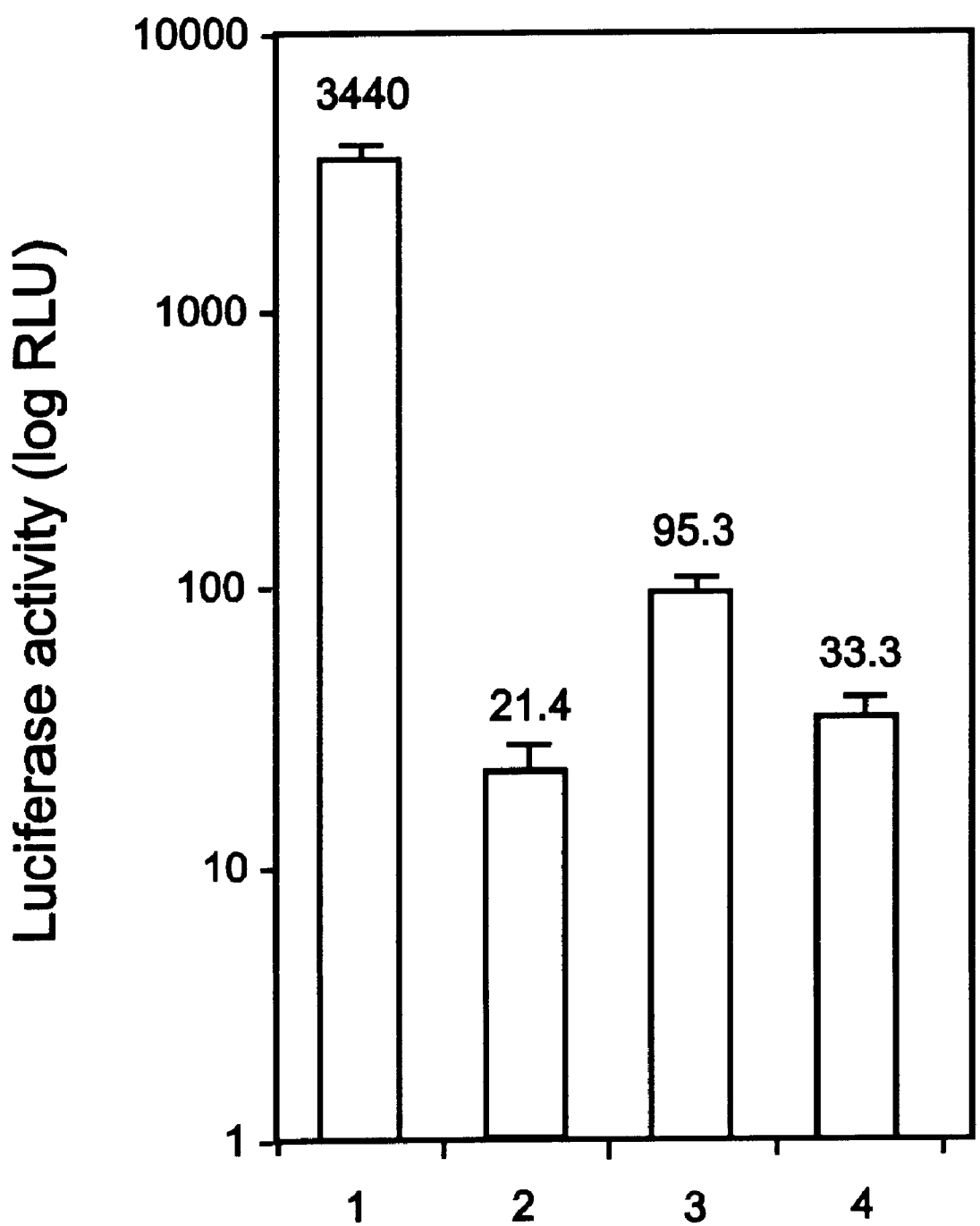
FIG. 4 shows the results of luciferase repression assays of transiently transfected CHO-K1 cells. All cells were transfected with the reporter plasmid (pRSVO-luc) and co-transfected with vector (mock), pCMV-lacI, pCMV-APPI and pCMV-ISRP cDNA's in lanes 1–4, respectively. Luciferase assays were performed on whole cell extracts, and the average relative light units from three transfection experiments are plotted ±SEM. All co-transfected lacI-encoding plasmids repress luciferase activity 35–150-fold.
Figure 5:
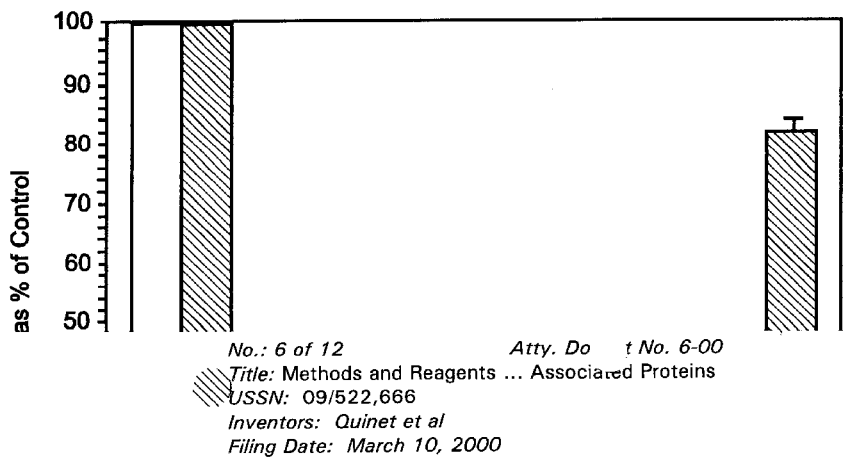
FIG. 5 demonstrates that regulatory fatty acids modulate proteolytic processing of the LacI-SREBP fusion. Transfected cells were incubated in medium containing 5% LPDS alone or supplemented with oleate bound to albumin. Data represent the mean ±SEM of triplicate analyses.
Figure 5:
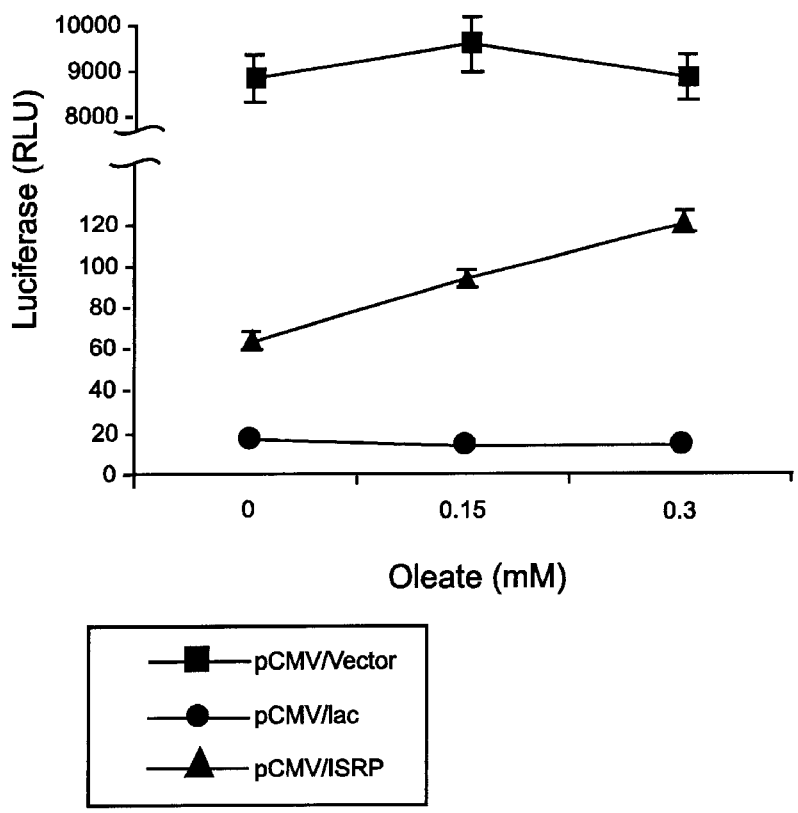

The LacSwitch II mammalian expression system (FIGS. 10A–C, Stratagene) is sensitive to the transcriptional repression of the bacterial lacI product. A luciferase cDNA was cloned into the lacd regulated promoter vector to create the reporter plasmid pRSVo-luc (FIG. 2C). Co-transfection of pRSVO-luc with a plasmid expressing lacI (pCMV-lacI) resulted in a marked inhibition of luciferase activity relative to the reporter alone (FIG. 4). This co-transfection serves as a control in the experiments described below.

Specific protease substrate fusion expression constructs were generated by PCR cDNA cloning. APP and SREBP were fused to lacI with a short C-terminal nuclear localization sequence (NLS) (See U.S. Pat. No. 5,776,689, incorporated herein by reference) and were named pCMY-APPI and pCMV-ISRP, respectively. All relevant processing sites and regulatory domains were retained in these constructs. These plasmids were engineered so that membrane-bound APP and SREBP proteolytic substrate "anchors" tether a cytosolic lacI to the ER. Proteolytic processing of these fusions liberates the repressor from membrane attachment, allowing its relocalization to the nucleus. See FIG. 2C for vector diagrams.

Figure 3:
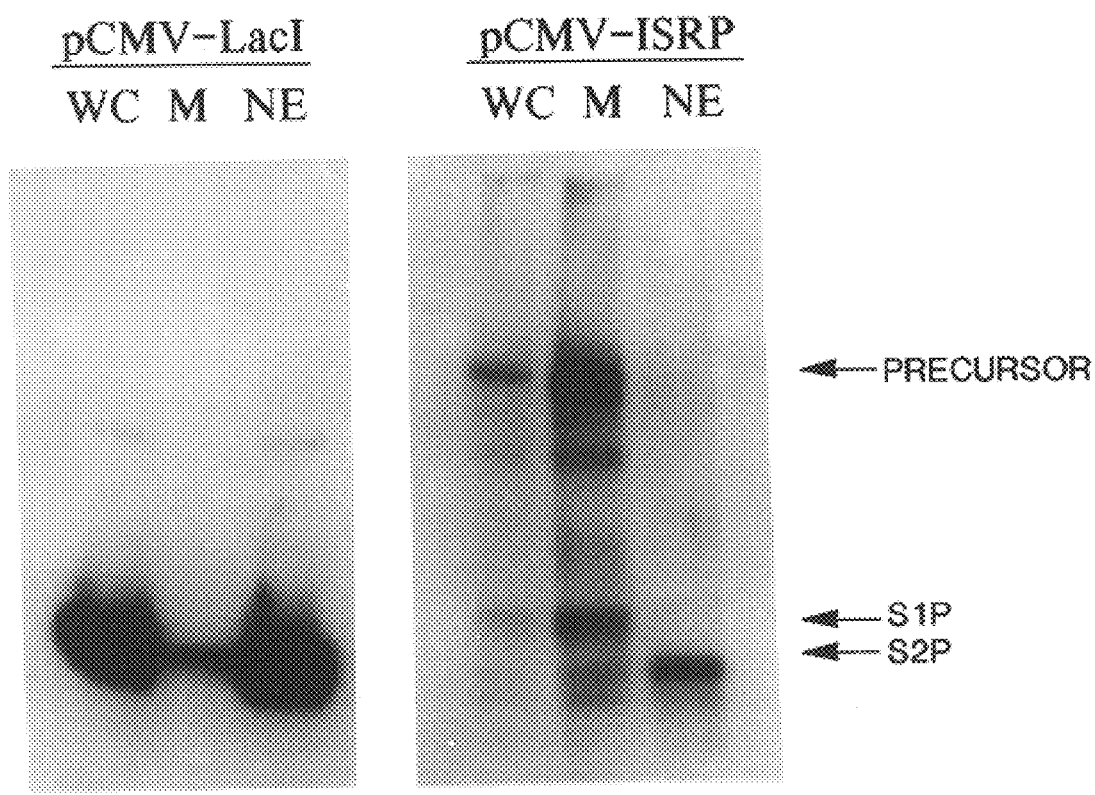
FIG. 3 demonstrates intracellular segregation of proteolytic substrate (precursor) and products. Immunoblot analysis of sub-cellular protein fractions isolated from cells transfected with lacI-containing expression constructs. Proteins were probed with anti-lacI antibodies. WC=whole cell lysate; M=membrane fraction; and NE=nuclear extract. S1P and S2P denote SREBP site 1 and site 2 protease cleavage products.

Western immunoblot analyses of sub-cellular fractions isolated from cells transfected with recombinant substrates were probed with anti-lacI antibodies. The control lacI transfection analysis displayed the expected 41 kd band, which exhibits marked nuclear segregation due to the efficient use of the NLS by the host CHO-K1 cells (FIG. 3). Conversely, appropriately sized precursors of 113 kd and 115 kd for APPI and ISRP fusions, respectively, were observed in the whole cell and membrane fractions, but were nearly absent from the nuclear extracts. Also, immunodetection of a nuclear signal of the expected size (42–43 kd; slightly larger than lacI-NLS) for each substrate is consistent with the assay theory and the reporter repression data presented below. This dramatic cellular segregation of precursors (membrane fraction) and cleavage products (nuclear extract) indicate that the fusion substrates were initially being localized to the ER.

Interestingly, discrete bands that are several kd larger than the expected lacI liberation products are observed in the membrane fractions for both the APPI and ISRP substrates. The apparent masses of these bands are consistent with lumenal APPI secretase ($\alpha$ and/or $\beta$) and ISRP site1 protease cleavage events. As one would predict, these lumenal cleavage products are retained in the ER and are released only following the sequential intrinsic hydrolysis by the $\gamma$-secretase and S2P, respectively. Other minor bands are observed, and without wishing to be bound by any particular theory, these are believed to represent non-specific degradation routes. Significantly, these bands remain within the membrane and should not affect the assay.

Transient co-transfection of the pRSVO-luc reporter with pCMV-APPI resulted in a 35 fold reduction in lucifernse activity relative to a mock co-transfection. Similarly, pCMV-ISRP co-transfection resulted in a 100 fold reduction in luciferase activity (FIG. 4). These levels of repression approach those of the control plasmid (pCMV-IacI). From these observations we conclude that the APP and SREBP lacI fusion substrates are, to a large extent, being localized to the ER where they are being processed correctly. As anticipated, the liberated lacI is released from the membrane and relocalizes to the nucleus via its NSL. In the nucleus, the lacI repressor protein functions to repress transcription from the reporter, thereby dramatically lowering luciferase activity.

Analyses of proteolytic processing events that occur within the lipid bilayer of cellular membranes or within the ER lumen have prven difficult to define oil a biochemical level. Several membrane associated protease assays utilizing recombinant substrates have been described. These include HMG-CoA reductase/$\beta$-galactosidase fusions [Lecureux and Wattenburg (1994) *J. Cell. Sci.* 107(Pt.9):2635–2642] and an ER tethered Gal4-protease fusion assay in yeast cells. Although these approaches offer certain advantages, they fail to provide an assay for both limenal and intrinsic membrane cleavage events that result in a signal suitable for direct high-throughput screening in mammalian cells. Our efforts were directed toward developing a cellular assay that fulfills these criteria while circumventing the need to clone the proteases of interest. We demonstrated that the repressor release assay of the present invention can specifically and efficiently monitor membrane associated proteolysis in mammalian cells.

The APP, Notch and SREBP maturation pathways were coupled to the suppression of reporter gene expression (See FIGS. 4 and 9). This forms the basis of a direct, high throughput compound screen without having to isolate the enzymes of interest. Quite simply, compounds that block any stage of the endogenous cell proteolytic processing of APP or SREBP also block the liberation of lacI from the membrane, leading to reporter expression. Note that the membrane release specific cleavage (within the transmembrane domain) is thought to follow prerequisite ER lumenal proteolytic events for both APP and SREBP substrates [Brown and Goldstein (1997) supra]. This property allows screeig of any target(s) acting at or prior to the membrane specific cleavage step that effects repressor release (i.e., γ-secretase, β-secretase, presenilin, etc. and S1P, S2P, SCAP, etc.). Compound "hits" are scored as increases in luciferase activity, encompassing a relatively wide screening window of 30–100 fold of reporter gene inducibility. This reporter readout offers a significant technical advantage over schemes that directly measure reduced cleavage efficiency as they circumvent such common screening pitfalls as signal quenchig, non-specific inhibitors of protein processing or gene expression, and toxicity of candidate inhibitors to general cellular processes. Also, the fact that both precursor and cleavage products are observed in cells suggests that this system is operating at an intermediate level of activity and should provide a window amenable to drug screening without extensive additional development.

We had been concerned that intact fision protein precursors could localize to the nucleus and repress reporter activity without being proteolyzed. Several lines of evidence indicate that this is not the case. The GRPSP is C-terminal to lacI in the pCMV-ISRP construct and its translational emergence from the ribosome would follow the NLS. Also, the lacI C-terminus is a sterically open structure [Lewis et al. (1996) Science 271:1247–1254] and could theoretically accommodate large fusions. It is, however, unlikely that intact ISRP-mediated repression is occurring to any significant degree as the membrane and nuclear localization patterns are consistent with initial ER localization followed by proteolysis and nuclear relocalization (FIG. 3). For the APP fusion substrate, the co-crystal structure of the lacI and lac operator would seem to preclude a fusion protein with a large N-terminal extension from binding DNA [Miller, J. (1996) Nature Struct. Biol. 3:310–312], indicating that processing is prerequisite to reporter (luciferase) repression. Also, the signal sequence translated from pCMV-APPI mRNA should dock the ribosome to the ER prior to the NLS synthesis [Simon, S. (1993) Curr. Opin. Cell. Biol. 5:581–588]. Again, the sub-cellular fractionation experiments demonstrate the membrane localization, proteolysis and relocalization theory of reporter repression.

Figure 6:
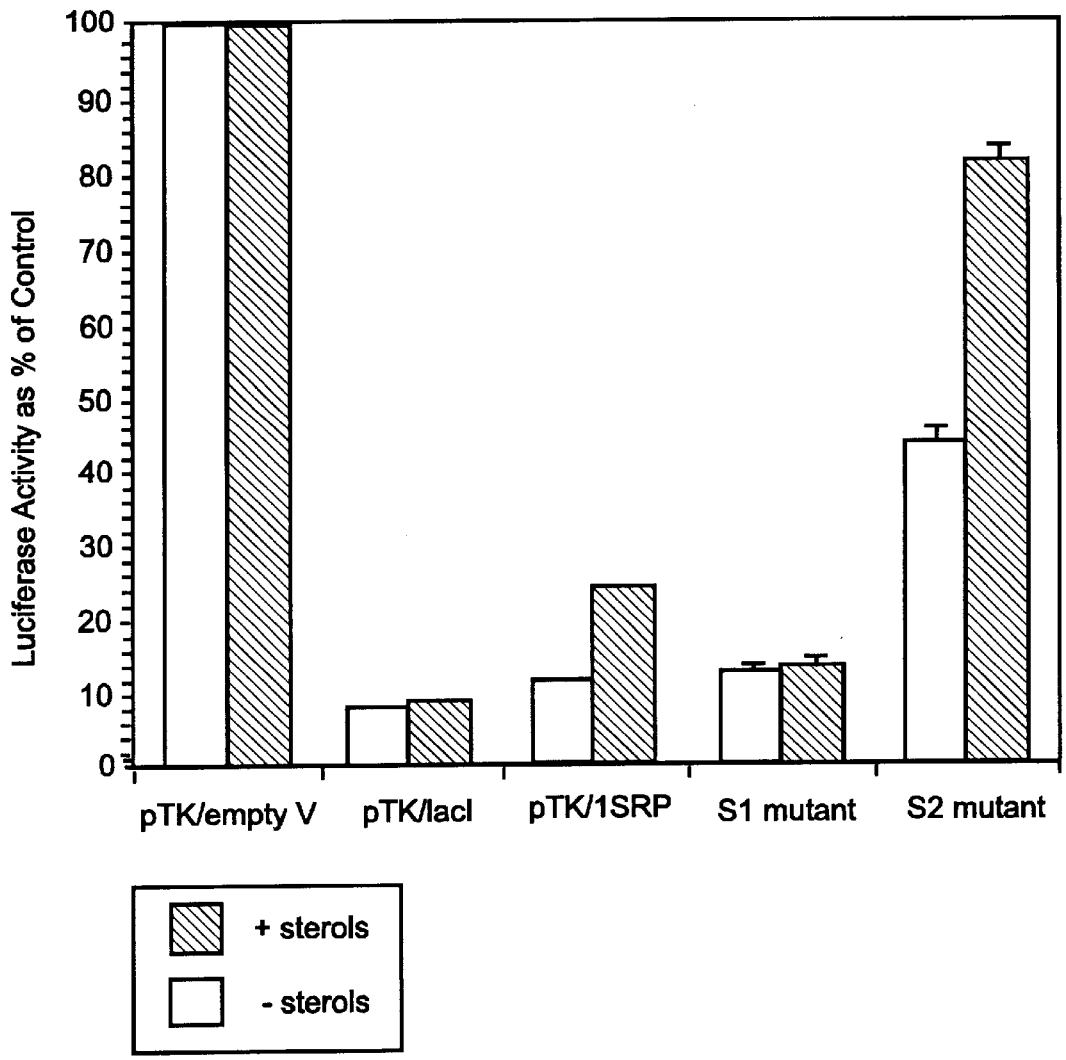
FIG. 6 shows sterol-regulated proteolysis and that a site 2 mutant inhibits sequence-specific cleavage. Cells were transfected with 0.2 μg of pRSVO-luc and 1.0 μg of "empty"

A more rigorous test of the proteolytic-dependence of luciferase repression includes an analysis of mutated SREBP2 substrates known to inhibit specific cleavage [Hua et al. (1996) supra; Sakai et al. (1996) supra]. These experiments utilize mutated site 1 and site 2 pCMV-ISRP templates and eliminates the possibility of non-specific proteolytic liberation of lacI from the ER. See FIG. 6, which demonstrates that mutations in either Site-1 protease or Site-2 protease recognition sites block repressor release and allow reporter readout.

As described above, the repressor release assay was developed primarily as a direct high-throughput cellular compound screen. These repressor release assays can also be used to assess the contributions of cloned accessory proteins to proteolysis, clonal protease candidate cDNAs or altered sequence specificity substrates by simple co-transfection experiments. Alternatively, compounds of interest are assayed for their effects on specific hydrolysis. It should be noted that this assay is easily adapted to assay soluble enzymes by engineering the proteolytic cleavage site on the cytosolic side of the membrane. Clearly, this type of assay format provides the flexibility for the adaptation of a wide variety of cellular protease assays.

The present inventors have developed an assay that monitors the proteolytic maturation pathway for proteins of interest. In one embodiment specifically exemplified herein, the proteolytic substrate of interest is SREBP-2 and the maturation pathway includes proteolysis by a membrane-associated protease. The assay is dependent on a lacI-regulated reporter gene readout (e.g., luciferase) and a SREBP-2/lacI fuision protein (ISREP) which is targeted to the endoplasmic reticulum. Proteolytic cleavage by tile membrane-associated protease releases the repressor, which then migrates to the nucleus, where it binds to the lac operator sequence upstream of the reporter coding sequence. Repressor binding prevents reporter expression. This technology couples the endogenous SREBP proteolytic processing activities residing in CHO-K1 cells to a reporter gene readout. The lac repressor (LacI) was tethered to the cytosolic face of the endoplasmic reticulum via its recombinant fusion to the N-terminus of SREBP2. This fusion essentially replaces the SREBP transcription activator with the lactose bacterial repressor while retaining all relevant SREBP processing signals, transmembrane domains and the regulatory C-terminus. A LacI-SREBP2 expression plasmid and a LacI responsive luciferase reporter were transiently co-transfected into CHO-K1 cells. Immunoblot analysis of sub-cellular fractions indicate that the LacI-SREBP2 fusion protein is expressed and properly localized to cellular membranes. Substrate-specific processing events release the lacI domain from the membrane allowing its nuclear relocalization which results in a dramatic 100-fold proteolytic-dependent repression of luciferase transcription. System validation experiments demonstrate that the SREBP "Repressor Release Assay" is sensitive to the DRSR-AS recognition site mutant of the SREBP site-2 protease (S2P) and also reveal that exposure to exogenous lipids (cholesterol and oleic acid) reduces processing consistent with the "cholesterol sensor" model of SREBP proteolysis. See FIGS. 4–7 and 9. Additionally, the small molecule MDL 28170 known to repress amyloid precursor protein (APP) maturation was shown to also inhibit the processing of the LacI-SREBP substrate, indicating that the S2P and γ-secretase proteases may be pharmacologically related. See FIG. 8.

The S2P protease cleaves the SREBP-2 protein within the transmembrane domain [Rawson et al. (1997) Molecular Cell. 1:47–57]. It has been reported that the Notch protein is cleaved within its transmembrane domain to release the intracellular domain of the Notch protein. This cleavage requires the presence of presenilin in mammalian cells, and it is sensitive to inhibitors of the γ-secretase protease [See, e.g., Wolfe et al. (1998) J. Med. Chem. 41:6–9].

Proteolytic enzymes of interest include, but are not limited to, SCAP, Site-1 protease (S1P), Site-2 protease and γ-secretase. Sterol-activated cleavage of SREBPs requires interaction with SCAP, the SREBP-cleavage activating protein and a postulated sterol sensor [Sakai et al. (1998) J. Biol. Chem. 273:5785–5793]. Critical amino acid residues critical for Site 1 and Site 2 proteolysis have been defined [Hua et al. (1996) supra]. The activation of SREBP bears a striking similarity to the maturation of the Alzheimer's precursor protein (APP) where in each case a prerequisite lumenal proteolytic cleavage event promotes subsequent intrinsic membrane proteolysis [Brown and Goldstein (1997) Cell 89:331–340].

The present repressor release assay allows the unambiguous, economical and efficient identification of test (candidate) compounds as inhibitors of membrane-associated proteases via reporter gene readout when that readout is greater in the presence than absence of the candidate compound. Pharmacological intervention of SREBP proteolytic processing events is of therapeutic value for the treatment of atherosclerosis, diabetes and obesity [Boizard et al. (1998) J. Biol. Chem. 273:29164–29171;

Shimomyra et al. (1998) *Genes Devel.* 12:3182–3194]. Pharmacological intervention in amyloid precursor protein processing can prevent the release of the amyloid protein to prevent or lessen the severity of Alzheimer's disease.

The recombinant host cells of the present invention comprise hybrid proteins containing polypeptides (i.e., repressor and regions) or fragments thereof having amino acid sequence lengths that are at least 25% (more preferably at least 50%, and most preferably at least 75%) of the length of a disclosed polypeptide (i.e., a polypeptide having an amino acid sequence as set forth in SEQ ID NO:2, SEQ ID NO:4 or SEQ ID NO:6), and have at least 60% sequence identity (preferably at least 75% identity; more preferably at least 85%, and most preferably at least 90% to 95% identity) with the disclosed polypeptides, where sequence identity is determined by comparing the amino acid sequences of the polypeptides when aligned so as to maximize overlap and identity while minimizing sequence gaps. Gaps are treated as mismatched amino acids. Also included in the present invention are polypeptides and fragments thereof that contain a segment comprising 6 or more (preferably 8 or more, more preferably 10 or more, and most preferably 12 or more) contiguous amino acids that shares at least 60% sequence identity (preferably at least 75% identity, more preferably at least 85% identity; and most preferably at least 90% to 95% identity) with any such segment of any of the disclosed polypeptides.

In particular, sequence identity may be determined using WU-BLAST (Washington University BLAST) version 2.0 software which builds upon WU-BLAST version 1.4, which in turn is based on the public domain NCBI-BLAST version 1.4 [Altschul and Gish (1996) in Doolittle, Ed., *Methods in Enzymology* 266:460–480; Altschul et al. (1990) *Journal of Molecular Biology* 215:403–410; Gish and States (1993) *Nature Genetics* 3:266–272; Karlin and Altschul (1993) *Proc. Natl. Acad. Sci. USA* 90:5873–5877; all of which are incorporated by reference herein]. WU-BLAST version 2.0 executable programs for several UNIX platforms can be downloaded from ftp://blast.wustl.edu/blast/executables. The complete suite of search programs (BLASTP, BLASTN, BLASTX, TBLASTN, and TBLASTX) is provided at that site, in addition to several support programs. WU-BLAST 2.0 is copyrighted and may not be sold or redistributed in any form or manner without the express written consent of the author; but the posted executables may otherwise be freely used for commercial, nonprofit, or academic purposes. In all search programs in the suite (BLASTP, BLASTN, BLASTX, TBLASTN and TBLASTX), the gapped alignment routines are integral to the database search itself, and thus yield much better sensitivity and selectivity while producing the more easily interpreted output. Gapping can optionally be turned off in all of these programs, if desired. The default penalty (Q) for a gap of length one is Q=9 for proteins and BLASTP, and Q=10 for BLASTN, but may be changed to any integer value including zero, one through eight, nine, ten, eleven, twelve through twenty, twenty-one through fifty, fifty-one through one hundred, etc. The default per-residue penalty for extending a gap (R) is R=2 for proteins and BLASTP, and R=10 for BLASTN, but may be changed to any integer value including zero, one, two, three, four, five, six, seven, eight, nine, ten, eleven, twelve through twenty, twenty-one through fifty, fifty-one through one hundred, etc. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

The present invention also includes polynucleotides that hybridize under reduced stringency conditions, more preferably stringent conditions, and most preferably highly stringent conditions, to polynucleotides described herein (i.e., the polynucleotides as depicted in SEQ ID NO:1, SEQ ID NO:3, or SEQ ID NO:5). Examples of stringency conditions are shown in the table below; highly stringent conditions are those that are at least as stringent as, for example, conditions A–F; stringent conditions are at least as stringent as, for example, conditions G–L; and reduced stringency conditions are at least as stringent as, for example, conditions M–R.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≥50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | ≥50 | 67° C.; 1xSSC -or- 45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | ≥50 | 70° C.; 1xSSC -or- 50° C.; 1xSSC, 50% formamide | 70° C.; 0.3xSSC |
| F | RNA:RNA | <50 | $T_F$*; 1xSSC | $T_F$*; 1xSSC |
| G | DNA:DNA | ≥50 | 65° C.; 4xSSC-or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | ≥50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | ≥50 | 70° C.;4xSSC-or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | ≥50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | ≥50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | ≥50 | 60° C.; 4xSSC -or- 45° C.; 6xSSC, 50% formamide | 60° C.; 2xSSC |
| R | RNA:RNA | <50 | $T_R$*; 4xSSC | $T_R$*; 4xSSC |

‡: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†: SSPE (1xSSPE is 0.15 M NaCl, 10 mM $NaH_2PO_4$, and 1.25 mM EDTA, pH 7.4) can be substituted for SSC (1xSSC is 0.15 M NaCl and 15 mM sodium citrate) in the hybridization and wash buffers; washes are performed for 15 minutes after hybridization is complete.
*$T_B$ –$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$ (° C.) = 2(# of A + T bases) + 4(# of G + C bases). For hybrids between 18 and 49 base pairs in length, $T_m$ (° C.) = 81.5 + 16.6($\log_{10}$[$Na^+$]) + 0.41(% G + C) – (600/N), where N is the number of bases in the hybrid, and [$Na^+$] is the concentration of sodium ions in the hybridization buffer ([$Na^+$] for 1xSSC = 0.165 M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Pro-* tocols in Molecular Biology, 1995, F. M. Ausubel et al., eds., John Wiley & Sons, Inc., sections 2.10 and 6.3–6.4, incorporated herein by reference.

Preferably, each such hybridizng polynucleotide has a length tat is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

A further aspect of the invention includes vectors comprising a DNA sequence as described above in operative association with an expression control sequence. Regulatory sequences for such vectors are known to those skilled in the art and may be selected depending upon the host cells and the repressor protein. Such selection is routine and does not form part of the present invention. These vectors may be employed in a novel process of the present invention in which a cell line transformed with a DNA sequence encoding a transcription repressing region and a protease cleavage region, or biologically active fragments thereof, in operative association with an expression control sequence, is cultured under suitable conditions for growth. The resulting modified host cells can be placed in a growth medium, which optionally contains agar, with the test sample applied to the growth medium. The growth medium is preferably a conventional liquid medium of growth reagents and water, such as DMEM. As discussed above, this process can employ a number of known cultured eukaryotic cells, as host cells for expression of the polypeptide. In the present methods, mammalian host cells are preferred.

In order to illustrate the invention, description of preferred embodiments are presented herein. Specific embodiments employ the DNA constructs pCMV-APPI, pCMV-NotI, pCMV-ISREP, and pTMI. The expression plasmids were transfected into a mammalian host cell, as specifically exemplified, CHO-K1 cells. Disruption, or blocking, of the proteolytic activity prevents the cleavage of the repressor portion of the chimeric proteolytic substrate protein, which is desirably either membrane bound or wtlen ihe lumen of the ER, and the reporter gene is expressed in the absence of a proteolytically released repressor.

A variety of alternative embodiments and variations will be apparent to those of skill in the art, including alternative host cells (e.g., mammalian, fungal, yeast, insect, amphibian and the like), alternative reporter genes, variations of the basic repressible reporter gene, variations in the transcription regulatory sequences controlling the expression of the reporter gene, and others. Moreover, in addition to highthroughput screening for potential modulators (inhibitors) of a particular target protease, the present invention can be adapted to a number of additional uses, such as to further define protease recognition sequences in proteins, to characterize analogs, and to evaluate candidate compounds generated in structure-activity-relationship programs or using combinatorial chemistry. These variations, modifications, and additional applications constitute part of the present invention.

Monoclonal or polyclonal antibodies, preferably monoclonal, specifically reacting with a protein or protein region encoded by a particular coding sequence, may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1995) vide infra.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N. Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York, and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

All references cited in the present application are incorporated by reference hereinto the extent that there is no inconsistency with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Construction of Recombinant Plasmids

Molecular Reagents: Generation of recombinant plasmids employed standard molecular techniques. Oligonucleotides were prepared on an ABI automated synthesizer (Perkin Elmer Cetus, Norwalk, Conn.) with specific sequences detailed below. Polymerase chain reactions (PCR) employed standard techniques [Finney M. (1993) *Current Protocols in Molecular Biology*, Wiley & Sons, NY]. Recombinant plasmids were transfected into DH5α competent *E. coli* cells (GIBCO Life Technologies, Rockville, Md.), following manufacturer's instructions. Recombinant plasmid stocks were prepared using Qiagen Mini preps (Qiagen, Valencia, Calif.). DNA sequencing was performed using dye-deoxy terminator reactions (Perkin Elmer Cetus, Norwalk, Conn.) and an ABI 373 automated sequencer (Applied Biosystems, Foster City, Calif.).

To construct the reporter plasmid (pRSVO-luc), luciferase cDNA was isolated from pGL3 (Promega, Madison, Wis.) on a 1.65 kb XhoI-XbaI restriction endonuclease fragment and cloned directionally between the XhoI and XbaI sites of pOPRSVI/MCS, Lac operator vector (Stratagene, La Jolla, Calif.). This plasmid contains two lac operators, one within the RSV-LTR promoter and another in the 5'-untranslated intron, which coordinately repress reporter gene expression in the presence of the lacI gene product (i.e., the lacI repressor protein).

pCMV-APPI was constructed by fusing two PCR products: APP (amino acids 1–651) with the lacI-NLS (amino acids 1–373) of pCMV-lacI, Lac repressor vector (Stratagene). These were fused in frame at a uniquely engineered restriction site (BspEI) within a small flexible linker (GlySerGly). The APP PCR product was synthesized with the primers GCAAGCTTCCACCATGCTGCCCG-GTTTGGCAC (SEQ ID NO:12) and GCTCCGGATC-CTTTCTTCTTCAGCATCACC (SEQ ID NO:13) were used to generate a 1.9 kb APP fragment by pfu polymerase (Stratagene) PCR using pcDNA1-APP695 as template. See Kang et al. (1987) *Nature* 325:733–736 for a description of the APP cDNA template [See also Genbank #Y00264]. The 1.9 kb PCR product spans sequences from the start codon of the signal sequence through the LysLysLys stop transfer signal immediately following the transmembrane domain at amino acid position 651. The LacI-NLS fragment was synthesized using the primers GCTCCGGACCAG-TAACGTTATACGATGTCG (SEQ ID NO:14) and GCTCTAGATCAAACCTTCCTCTTCTTCTTAGG (SEQ ID NO:15) from the pCMV-lacI template, resulting in a 1.1 kb product. Each PCR product was individually cloned into the EcoRV site of bluescript pSK(–) and named pSK-APP and pSK-lacIA, respectively. The expression vector pcDNA3.1-Zeo(+) (Invitrogen) was restricted with HindIII and Xbal. pSK-APP was restricted with HindIII and BspEI. pSK-LacIA was restricted with BspEI and XbaI. All fragments were isolated and included in a 3-way ligation, resulting in the plasmid pCMV-APPI. This construct is translated into the ER via its signal sequence [Simon, S. (1996) supra] with the C-terminal lacI-NLS remaining cytosolic. The nucleotide sequence encoding the APP chimeric repressor construct is given in Table 1. See also SEQ ID NOs:1 and 2.

The pCMV-ISRP clone (encoding the LacI-SREBP fusion protein) was designed to replace the SREBP -terminal transcription activator domain (amino acids 1–472) with the lacI-NLS (amino acids 3–373) of pCMV-lacI (Stratagene). PCR-amplified sequences encoding amino acids 473–1142 of SREBP2 were fused in frame with a LacI-NLS amplimer at a uniquely engineered restriction site (BspEI) within a small flexible linker sequence (Gly-Ser-Gly), encoded by GGATCCGOA. PCR-deved sequences were confirmed by DNA sequencing.

The pCMV-ISRP clone was constructed as a fusion of two PCR products and a cloned restriction fragment. Essentially the SREBP -terminal ranscription activator domain has been replaced by lacI-NLS with the same Gly-Ser-Gly linker fusing the SREBP and lacI sequences. The C-terminal portion of human SREBP2 [Genbank #HSU02031] was derived from the pACT2-SRFBP2 fusion construct described elsewhere. This plasmid harbors the human SREBP2 cDNA sequences spanning nucleotide positions 1780–3544. Sequences corresponding to nucleotides 1533–1866 of SREBP2 were amplified by pfu PCR using the primers CTCCGGAGCGCTGGGCATGGTAGACC (SEQ ID NO:16) and GGCGAGATCCAGATCTGC (SEQ ID NO:17) with the human EST clone [Genbank #HSC2CS091] serving as template. The resultant 0.33 kb product was isolated. The LacI-NLS fragment was synthesized from the pCMV-lacI template using the primers CGG-TACCACCATGAAACCAGTAACG (SEQ ID NO:18) and CTCCGGATCCAACCTTCCTCTTCTTCTTAGG (SEQ ID NO:19) and the 1.1 kb product was isolated. These two PCR products were subcloned into the EcoRV site of bluescript pSK- and named pSK-0.33 and pSK-LacIS, respectively. Four restriction fragments were then isolated: the 1.1 kb Kpn1-BspE1 fragment from pSK-LacIS, the 0.33 kb BspE1-Bg1II fragment from pSK-0.33, a 1.7 kb Bg1II-XhoI fragment from pACT2-SREBP, and pcDNA3.1-Zeo(+) vector restricted with Kpn1 and XhoI. These were ligated in a four-way reaction to generate pCMV-ISRP that includes amino acids 473–1142 of SREBP2 fused to the C-terminal end of lacI-NLS. This construct should be translated in the cytoplam and insert itself into the ER as a "multi-pass" membrane protein [Hartman et al. (1989) *Proc. Natl. Acad Sci. USA* 86:5786–5790] with the N-terminal lacI-NLS and the C-terninal regulatory domains both remaining cytosolic. PCR-derived sequences were confirmed by sequencing.

Coding sequence and amino acid sequence information for the pCMV-ISRP chimeric proteolytic substrate protein are given in Tables 3 and 4 and in SEQ ID NOs:5 and 6.

The tk promoter was isolated from pTK-HSV-BP2 (Accession No. 99530, American Type Culture Collection, Manassas, Va.) by PCR amplification and inserted into the NruI/NheI sites of pCMV-ISRP, thus replacing the CMV promoter. The site 1 (R519A) and site 2 (DRSR478AS) mutant ISRP templates were generated using the Quick-Change protocol of Stratagene, and the desired sequences were confirmed by DNA sequencing.

pCMV-NotI cloning. The pCMV-NotI plasmid contains a fusion of three separate components: the mouse notch signal peptide coding sequence, the deleted rat notch coding sequence including the transmembrane domain (TM), and the lacI repressor coding sequence. This construction is based on the Notch ΔE template [Struhl and Adachi (1998) *Cell* 93:649–660] where the large extracellular domain coding sequence containing the EGF repeat's coding sequence is deleted, and the C-terminal coding region is replaced with a Ga14-VP16 transcriptional activator coding sequence. The only difference is that the activator domain sequence has been replaced with lacI sequence. Briefly, both strands encoding the first 21 amino acids of the mouse notch signal peptide were synthesized as oligonucleotides and annealed. (Top strand: AGCTTCCACCATGCCACG-GCTCCTGACGCCCCTTCTCTGC-CTAACGCTGCTGCCCGC GCGCGCCGCAAGAGGC; (SEQ ID NO:20). Bottom strand: GCCTCTTGCG-GCGCGCGCGGGCAGCAGCGTTAGGCA-GAGAAGGGGCGTCAGGAGCC GTGGCATGGTGGA; (SEQ ID NO:21). The notch TM domain was cloned from a λgt11 rat hippocampal cDNA library (Stratagene) by PCR using as a 5' primer CAGCCTCAATATTCCCTACAA-GATCG (SEQ ID NO:22) and as a 3' primer TCAGGTC-CGGATCCGCGCTTGCGGGACAGCAGCACC (SEQ ID NO:23)). This PCR product was fused in frame to the naturally occurring SspI site of the mouse notch clone and includes the entire TM domain ending at the stop transfer sequence. These DNA fragments were inserted into a LacI-containing HindIII/BspEI restricted pCMV-APPI vector fragment in a 3-way ligation to generate pCMV-NotI. Transfection and analyses of this plasmid were as described.

Coding sequence information for the NotI chimeric proteolytic substrate is given in Table 2. See also SEQ ID NOs:3 and 4.

pTMI cloning. The first 29 amino acids of P450 (MDPVVVLGLCLSCLLLLSLWKQSYGGGKL, amino acids 1–29 of SEQ ID NO:10) have been shown to function as a signal/TM sequence that localizes and remains largely in the ER membranes [Szczesna-Skorupa et al. (1998) *PNAS* 95:14793–14798; Sakai et al. (1998) supra]. (See also SEQ ID NOs:8 and 9.) Both strands of this sequence, with the addition of a Kozak sequence, and flanking cloning sites were synthesized and annealed (Top strand: AGCTTCCAC-CATGGACCCTGTGGTGGT-GCTGGGGCTCTGTCTCTCCTGTTTGCTTCTC CTTTCACTCTGGAAACAGAGCTATGGGG-GAGGGAAACTTGGAT; SEQ ID NO:24, and Bottom strand: CCGGATCCAAGTTTCCCTCCCCCAT-AGCTCTGTTTCCAGAGTGAAAGGAGAAGCAAA CAGGAGAGACAGAGCCCCAGCACCACCA-CAGGGTCCATGGTGGA; SEQ ID NO:25). The resulting dsDNA fragment was inserted into a HindIII/BspE1 restricted pCMV-APPI vector as described for pCMV-NotI above, resulting in a 29 amino acid P450 membrane tether coding sequence fused in-frame to a cytosolic LacI coding sequence with a 3 amino acid G-S-G linker coding sequence (encoded by GGATCCGGA). The GSG linker coding sequence comprises the BspEI site. The lacI sequence follows the BspEI site.

pTMI-C3 cloning. Two synthetic caspase-3 sites spaced with G-S-G linkers (GSG-DEVD-GSG-DEVD-GSG, SEQ ID NO:27) were cloned into the BspEI site of pTMI. The nucleotide sequence encoding this protein segment is GOATCCOGAGATOAAGTGGACGGATC-COGAGATGAMGTGGACGATGAAGTGGACG GATC-CGGAGATGAAGTGGAC SEQ ID NO:26. This plasmid encodes a fusion protein harboring two cytosolic caspase-3 sites located between the P450 TM tether and the lacI region. It is named pTMI-C3. This plasmid was constructed by inserting the dsDNA fragment obtained from the annealed oligonucleotides; (Top strand: CCGGAGATGAAGTG-GACGGATCAGGTGATGAAGTGGACGGAT; SEQ ID NO:28 and Bottom strand: CCGGATCCGTCCACTTCAT-CACCTGATCCGTCCACTTCATCT; SEQ ID NO:29) into a pTMI BspEI-restricted vector.

Example 2

Cell Culture, Transfections and Luciferase Assays.

CHO-K1/HEK 293 cells were cultured in whole media (DMEM with 10% fetal bovine serum and 0.1 mM proline) at 37° C. in a 5% $CO_2$ atmosphere. Approximately $3 \times 10^5$ cells were plated into 6 well dishes (35-mm) 24 hrs prior to transfection. Cells were transiently transfected with 2 µg of plasmid DNA (1 µg of pRSVO-luc and 1 µg of mock vector DNA or LacI encoding plasmids) complexed with 20 µg Lipofectamine reagent as recommended by Gibco-BRL (Gaithersburg, Md.). The cells were washed once and covered in 0.8 ml OPTI-MEM medium. The DNA-lipid preparation was layered onto these cells and incubated at 37° C. for five hrs. This transfection mixture was replaced with 2.5 ml whole medium and the cells incubated for an additional 36–48 hrs at 37° C. prior to analysis. When preparative 100 mm dishes were used, the above volumes and masses were multiplied by a factor of six. Transfection efficiencies were generally 30–50%.

In some experiments, MDL 28170 was incubated with the transfected cells for approximately 36 hrs to allow for LacI-SREBP processing equilibration. CHO-K1 cells can be obtained from the American Type Culture Collection, Manassas, Va., as Accession No. CRL-61.

Luciferase assays were performed as described by Promega (Madison, Wis.). The transfected cells in each well were lysed with 0.5 ml of 1× Reporter lysis Buffer (Promega), and cell lysates were daluted to ensure linear analyses in an automated ML 1000 Luminometer (Dynatech Laboratories). Luciferase measurements are expressed as relative light units.

Example 3

Sub-Cellular Fractionation and Immunoblot Analysis.

Membrane and nuclear extracts were fractionated from transiently transfected cells essentially as described by Sakai et al. (1998) *Molecular Cell* 2:505–514. 100 mm dishes of CHO-K1 cells were cultured and transfected as described above. 48 hours post-transfection, the medium was aspirated and the cells washed 1× with PBS. The cells were scraped from the plates, and the cells were allowed to swell in 2 mls of hypotonic buffer A (10 mM Hepes-KOH at pH 7.4, 10 mM KCl, 1.5 mM $MgCL_2$, 1 mM sodium EDTA, 1 mM sodium EGTA, 1 mM dithiothreitol, and a protease inhibitor cocktail (Boelringer Mannheim)). After a 30 minute incubation on ice, the cells were passed through a 22-gauge needle 20 times prior to centrifugation at 1000×g for 5 minutes at 4° C. The supernatant was recentrifuged at 100,000×g for 30 minutes at 4° C. in a Beckman TLA 120.2 rotor, and the pellet was dissolved in 0.1 ml of SDS lysis buffer (10 mM Tris-HCl at pH 6.8; 100 mM NaCl, 1% (v/v) SDS, 1 mM EDTA, and 1 mM EGTA) and designated the membrane fraction. The pellet from the original 1000×g was resuspended in 0.1 ml of buffer B (10 mM Hepes-KOH at pH 7.4, 0.42 M NaCl, 2.5% (v/v) glycerol, 1.5 mM $MgCl_2$, 1 mM EDTA, 1 mM EGTA, 1 mM dithiothreitol, and a protease inhibitor cocktail (Boehringer-Mannheim)). The suspension was rotated at 4° C. for 1 hour and centrifuged at top speed in a microcentrifuge for 15 minutes at 4° C. The supernatant is designated as the nuclear extract fraction.

Samples of nuclear extract, membrane, and whole cell lysates (generally 5–25 µg) were denatured in SDS loading buffer and electrophoresed in 10%–20% SDS-polyacrylamide gradient gels. Separated proteins were transferred to PVDF membranes (Novex, San Diego, Calif.) for immunodetection using a commercially available LacI-specific polyclonal antibody (Stratagene) with an ECL detection system (Amersham, Arlington Heights, Ill.).

Proteins were electro-blotted (Biorad) and the filters were blocked for 2 hrs with 5% dry milk in PBS +0.3% Tween (PBS-T). A 1:1000 dilution of the lacI antibody added to the 5% dry milk in PBS-T for 2–18 hours. Following three 10 min PBS-T washes, this primary antibody was detected by incubating the filter with a 1:2000 dilution of donkey anti-rabbit horseradish peroxidase-conjugated IgG for 1 hr in PBS-T. Following three PBS-T washes, antibody staining was developed with the ECL substrate as recommended (Amersham), and the blots were exposed to Hyperfilm-MP (Amersham) for 10–60 sec. The primary antibody detects lacI epitopes found in the APP- and SREBP-lacI full-length fusion proteins as well as the proteolytic products containing the lacI sequences.

Example 4

MDL 28710 Pharmacology.

To confirm the applicability of the repressor release assay of the present invention, the following experiment was carried out with a known inhibitor of γ-secretase, MDL 28710. γ-secretase is recognized as a critical proteolytic processing enzyme in the maturation of APP.

10 cm dishes of CHO-K1 cells were transfected with equal masses of pCMV-APPI and pRSVO-luc as described above. After 24 hrs the cells were resuspended and transferred to opaque 96-well dishes at a final density of 300 cells/well. Note that this medium was complete except for the fact that it lacked phenol red dye. Immediately following the transfer, the MDL28710 candidate compound was added to concentrations of 0–30 µg/ml. This incubation was continued for 36 hrs, and samples were assayed for luciferase activity as described above.

TABLE 1

Coding Sequence of the APPI-LacI Fusion Protein from pCMV-APPI
(See also SEQ ID NOs: 1 and 2).

```
aagcttccaccatgctgcccggtttggcactgctcctgctggccgcctggacggctcgggcgctggaggtacccactgatgg
taatgctggcctgctggctgaaccccagattgccatgttctgtggcagactgaacatgcacatgaatgtccagaatgggaag
tgggattcagatccatcagggaccaaaacctgcattgataccaaggaaggcatcctgcagtattgccaagaagtctaccctg
aactgcagatcaccaatgtggtagaagccaaccaaccagtgaccatccagaactggtgcaagcggggccgcaagcagtgcaa
gacccatccccactttgtgattccctaccgctgcttagttggtgagtttgtaagtgatgcccttctcgttcctgacaagtgc
aaattcttacaccaggagaggatggatgtttgcgaaactcatcttcactggcacaccgtcgccaaagagacatgcagtgaga
agagtaccaacttgcatgactacggcatgttgctgccctgcggaattgacaagttccgaggggtagagtttgtgtgttgccc
actggctgaagaaagtgacaatgtggattctgctgatgcggaggaggatgactcggatgtctggtggggcggagcagacaca
gactatgcagatgggagtgaagacaaagtagtagaagtagcagaggaggaagaagtggctgaggtggaagaagaagaagccg
atgatgacgaggacgatgaggatggtgatgaggtagaggaagaggctgaggaaccctacgaagaagccacagagagaaccac
cagcattgccaccaccaccaccaccacacagagtctgtggaagaggtggttcgagttcctacaacagcagccagtaccccct
gatgccgttgacaagtatctcgagacacctggggatgagaatgaacatgcccatttccagaaagccaaagagaggcttgagg
ccaagcaccgagagagaatgtcccaggtcatgagagaatgggaagaggcagaacgtcaagcaaagaacttgcctaaagctga
taagaaggcagttatccagcatttccaggagaaagtggaatctttggaacaggaagcagccaacgagagacagcagctggtg
gagacacacatggccagagtggaagccatgctcaatgaccgccgccgcctggccctggagaactacatcaccgctctgcagg
ctgttcctcctcggcctcgtcacgtgttcaatatgctaaagaagtatgtccgcgcagaacagaaggacagacagcacaccct
aaagcatttcgagcatgtgcgcatggtggatcccaagaaagccgctcagatccggtcccaggttatgacacacctccgtgtg
atttatgagcgcatgaatcagtctctctccctgctctacaacgtgcctgcagtggccgaggagattcaggatgaagttgatg
agctgcttcagaaagagcaaaactattcagatgacgtcttggccaacatgattagtgaaccaaggatcagttacggaaacga
tgctctcatgccatctttgaccgaaacgaaaaccaccgtggagctccttcccgtgaatggagagttcagcctggacgatctc
cagccgtggcattcttttggggctgactctgtgccagccaacacagaaaacgaagttgagcctgttgatgcccgccctgctg
ccgaccgaggactgaccactcgaccaggttctgggttgacaaatatcaagacggaggagatctctgaagtgaagatggatgc
agaattccgacatgactcaggatatgaagttcatcatcaaaaattggtgttctttgcagaagatgtgggttcaaacaaggt
gcaatcattggactcatggtgggcggtgttgtcatagcgacagtgatcgtcatcaccttggtgatgctgaagaagaaaggat
ccggaCCAGTAACGTTATACGATGTCGCAGAGTATGCCGGTGTCTCTTATCAGACCGTTTCCCGCGTGGTGAACCAGGCCAG
CCACGTTTCTGCGAAAACGCGGGAAAAAGTGGAAGCGGCGATGGCGGAGCTGAATTACATTCCCAACCGCGTGGCACAACAA
CTGGCGGGCAAACAGTCGTTGCTGATTGGCGTTGCCACCTCCAGTCTGGCCCTGCACGCGCCGTCGCAAATTGTCGCGGCGA
TTAAATCTCGCGCCGATCAACTGGGTGCCAGCGTGGTGGTGTCGATGGTAGAACGAAGCGGCGTCGAAGCCTGTAAAGCGGC
GGTGCACAATCTTCTCGCGCAACGCGTCAGTGGGCTGATCATTAACTATCCGCTGGATGACCAGGATGCCATTGCTGTGGAA
GCTGCCTGCACTAATGTTCCGGCGTTATTTCTTGATGTCTCTGACCAGACACCCATCAACAGTATTATTTTCTCCCATGAAG
ACGGTACGCGACTGGGCGTGGAGCATCTGGTCGCATTGGGTCACCAGCAAATCGCGCTGTTAGCGGGCCCATTAAGTTCTGT
CTCGGCGCGTCTGCGTCTGGCTGGCTGGCATAAATATCTCACTCGCAATCAAATTCAGCCGATAGCGGAACGGGAAGGCGAC
TGGAGTGCCATGTCCGGTTTTCAACAAACCATGCAAATGCTGAATGAGGGCATCGTTCCCACTGCGATGCTGGTTGCCAACG
ATCAGATGGCGCTGGGCGCAATGCGCGCCATTACCGAGTCCGGGCTGCGCGTTGGTGCGGATATCTCGGTAGTGGGATACGA
CGATACCGAAGACAGCTCATGTTATATCCGCCGTTAACCACCATCAAACAGGATTTTCGCCTGCTGGGGCAAACCAGCGTG
GACCGCTTGCTGCAACTCTCTCAGGGCCAGGCGGTGAAGGGCAATCAGCTGTTGCCCGTCTCACTGGTGAAAAGAAAAACCA
CCCTGGCGCCCAATACGCAAACCGCCTCTCCCCGCGCGTTGGCCGATTCATTAATGCAGCTGGCACGACAGGTTTCCCGAC
```

TABLE 1-continued

Coding Sequence of the APPI-LacI Fusion Protein from pCMV-APPI
(See also SEQ ID NOs: 1 and 2).

T
GGAAAGCGGGCAGAGCAGCCTGAGGCCTCCTAAGAAGAAGAGGAAGGTTTGATCTAGA

Coding sequence from ATG at nucleotides 12–14 through
a TGA at nucleotides 3084–3086.

TABLE 2

Coding Sequence of the NotchI-Lac Fusion Protein Information
from pCMV-NotI (See also SEQ ID NOs:3 and 4).

AAGCTTCCACCATGCCACGGCTCCTGACGCCCCTTCTCTGCCTAACGCTGCTGCCCGCGCGCGCC

GCAAGAGGCATTCCCTACAAGATCGAAGCCGTAAAGAGTGAGACGGTGGAGCCTCCGCTGCCCTC

ACAGCTGCACCTCATGTACGTGGCGGCAGCTGCCTTCGTGCTCCTGTTCTTTGTGGGCTGTGGGG

TGCTGCTGTCCCGCAAGCGCGGATCCGGACCAGTAACGTTATACGATGTCGCAGAGTATGCCGGT

GTCTCTTATCAGACCGTTTCCCGCGTGGTGAACCAGGCCAGCCACGTTTCTGCGAAAACGCGGGA

AAAAGTGGAAGCGGCGATGGCGGAGCTGAATTACATTCCCAACCGCGTGGCACAACAACTGGCGG

GCAAACAGTCGTTGCTGATTGGCGTTGCCACCTCCAGTCTGGCCCTGCACGCGCCGTCGCAAATT

GTCGCGGCGATTAAATCTCGCGCCGATCAACTGGGTGCCAGCGTGGTGGTGTCGATGGTAGAACG

AAGCGGCGTCGAAGCCTGTAAAGCGGCGGTGCACAATCTTCTCGCGCAACGCGTCAGTGGGCTGA

TCATTAACTATCCGCTGGATGACCAGGATGCCATTGCTGTGGAAGCTGCCTGCACTAATGTTCCG

GCGTTATTTCTTGATGTCTCTGACCAGACACCCATCAACAGTATTATTTTCTCCCATGAAGACGG

TACGCGACTGGGCGTGGAGCATCTGGTCGCATTGGGTCACCAGCAAATCGCGCTGTTAGCGGGCC

CATTAAGTTCTGTCTCGGCGCGTCTGCGTCTGGCTGGCTGGCATAAATATCTCACTCGCAATCAA

ATTCAGCCGATAGCGGAACGGGAAGGCGACTGGAGTGCCATGTCCGGTTTTCAACAAACCATGCA

AATGCTGAATGAGGGCATCGTTCCCACTGCGATGCTGGTTGCCAACGATCAGATGGCGCTGGGCG

CAATGCGCGCCATTACCGAGTCCGGGCTGCGCGTTGGTGCGGATATCTCGGTAGTGGGATACGAC

GATACCGAAGACAGCTCATGTTATATCCCGCCGTTAACCACCATCAAACAGGATTTTCGCCTGCT

GGGGCAAACCAGCGTGGACCGCTTGCTGCAACTCTCTCAGGGCCAGGCGGTGAAGGGCAATCAGC

TGTTGCCCGTCTCACTGGTGAAAAGAAAAACCACCCTGGCGCCCAATACGCAAACCGCCTCTCCC

CGCGCGTTGGCCGATTCATTAATGCAGCTGGCACGACAGGTTTCCCGACTGGAAAGCGGGCAGAG

CAGCCTGAGGCCTCCTAAGAAGAAGAGGAAGGTTTGATCTAGA

Coding sequence from ATG at nucleotides 12–14 through a
TGA at nucleotides 1335–1337.

TABLE 3

ISRP nucleotide sequence from KpnI restriction site to XhoI restriction site as
described in Example 1. See also SEQ ID NO:3.

GGTACCACCATGAAACCAGTAACGTTATACGATGTCGCAGAGTATGCCGGTGTCTCTTATCAGACCGTTTCCCGCGTGGTGAACCAGGCCAG

CCACGTTT 100

CTGCGAAAACGCGGGAAAAAGTGGAAGCGGCGATGGCGGAGCTGAATTACATTCCCAACCGCGTGGCACAACAACTGGCGGGCAAACAGT

CGTTGCTGAT 200

TABLE 3-continued

ISRP nucleotide sequence from KpnI restriction site to XhoI restriction site as described in Example 1. See also SEQ ID NO:3.

TGGCGTTGCCACCTCCAGTCTGGCCCTGCACGCGCCGTCGCAAATTGTCGCGGCGATTAAATCTCGCGCCGATCAACTGGGTGCCAGCGTGG

TGGTGTCG 300

ATGGTAGAACGAAGCGGCGTCGAAGCCTGTAAAGCGGCGGTGCACAATCTTCTCGCGCAACGCGTCAGTGGGCTGATCATTAACTATCCGC

TGGATGACC 400

AGGATGCCATTGCTGTGGAAGCTGCCTGCACTAATGTTCCGGCGTTATTTCTTGATGTCTCTGACCAGACACCCATCAACAGTATTATTTTCT

CCCATGA 500

AGACGGTACGCGACTGGGCGTGGAGCATCTGGTCGCATTGGGTCACCAGCAAATCGCGCTGTTAGCGGGCCCATTAAGTTCTGTCTCGGCG

CGTCTGCGT 600

CTGGCTGGCTGGCATAAATATCTCACTCGCAATCAAATTCAGCCGATAGCGGAACGGGAAGGCGACTGGAGTGCCATGTCCGGTTTTCAAC

AAACCATGC 700

AAATGCTGAATGAGGGCATCGTTCCCACTGCGATGCTGGTTGCCAACGATCAGATGGCGCTGGGCGCAATGCGCGCCATTACCCGAGTCCGG

GCTGCGCGT 800

TGGTGCGGATATCTCGGTAGTGGGATACGACGATACCGAAGACAGCTCATGTTATATCCCGCCGTTAACCACCATCAAACAGGATTTTCGCC

TGCTGGGG 900

CAAACCAGCGTGGACCGCTTGCTGCAACTCTCTCAGGGCCAGGCGGTGAAGGGCAATCAGCTGTTGCCCGTCTCACTGGTGAAAAGAAAAA

CCACCCTGG 1000

CGCCCAATACGCAAACCGCCTCTCCCCGCGCGTTGGCCGATTCATTAATGCAGCTGGCACGACAGGTTTCCCGACTGGAAAGCGGGCAGAG

CAGCCTGAG 1100

GCCTCCTAAGAAGAAGAGGAAGGTTggatccggagCGCTGGGCATGGTAGACCGCTCACGGATTCTTCTGTGTGTCCTCACCTTCCTGTGCCTCT

CCTTT 1200

AACCCCCTGACTTCCCTGCTGCAGTGGGGAGGGCCCACGACTCTGACCAGCACCCACACTCAGGCTCTGGCCGCAGTGTCCTGTCATTCGA

GTCAGGTT 1300

CTGGGGGCTGGTTTGACTGGATGATGCCTACTCTTCTCTTATGGCTGGTAAATGGTGTGATTGTCCTGAGCGTCTTTGTGAAGCTGCTGGTTC

ATGGGGA 1400

GCCAGTGATCCGGCCACACTCGCGCTCCTCGGTCACCTTCTGGAGGCACCGGAAACAGGCAGATCTGGATCTCGCCAGAGGAGATTTTGCA

GCTGCTGCC 1500

GCCAACCTACAAAACCTGCCTGGCAGTTTTGGGCCGGGCACTGCCCACCTCCCGCCTGGACCTGGCCTGCAGCCTCTCCTGGAACGTGATCCG

CTACAGCC 1600

TGCAGAAGCTACGCCTGGTGCGCTGGCTGCTCAAGAAAGTCTTCCAGTGCCGGCGGGCCACGCCAGCCACTGAGGCAGGCTTTGAAAGACGA

AGCTAAGAC 1700

CAGCGCCCGGGATGCGGCTCTGGCCTATCACCGGCTGCACCAGCTGCACATCACAGGGAAGCTTCCTGCAGGATCCGCCTGTTCCGATGTAC

ACATGGCG 1800

TTGTGTGCCGTGAACCTGGCTGAATGTGCAGAGGAGAAGATCCCACCGAGCACACTGGTTGAGATCCATCTGACTGCTGCCATGGGCTCA

AGACCCGGT 1900

GTGGAGGCAAGCTGGGCTTCCTGGCCAGCTACTTCCTCAGCCGAGCCCAGAGCCTGTGTGGCCCCGAGCACAGTGCTGTTCCTGACTCCCTG

CGCTGGCT 2000

CTGCCACCCCCTGGGCCAGAAGTTTTTCATGGAGCGGAGCTGGTCTGTGAAGTCAGCTGCCAAGGAGAGTCTATACTGTGCCCAGAGGAAC

CCAGCTGAC 2100

TABLE 3-continued

ISRP nucleotide sequence from KpnI restriction site to XhoI restriction site as described in Example 1. See also SEQ ID NO:3.

CCCATTGCGCAGGTCCACCAGGCCTTCTGCAAGAACCTGCTGGAGCGAGCTATAGAGTCCTTGGTGAAACCTCAGGCCAAGAAGAAGGCTG

GAGACCAGG 2200

AAGAAGAGAGCTGTGAATTCTCCAGTGCTCTGGAGTACTTGAAATTACTTCATTCTTTTGTGGACTCTGTGGGGGTTATGAGCCCCCACTCT

CCAGGAG 2300

CTCCGTGCTCAAGTCCGCCCTGGGTCCAGACATCATCTGTCGGTGGTGGACGTCTGAATCACTGTGGCCATCAGCTGGCTCCAGGGAGACG

ATGCAGCT 2400

GTGCGCTCTCATTTTACCAAAGTGGAACGCATCCCCAAGGCCCTGGAAAGTGACAGAGAGCCCCCTGGTGAAGGCCATCTTCCATGCCTGCAG

AGCCATGC 2500

ATGCCTCACTCCCTGGGAAAGCAGATGGGCAGCAGAGTTCCTTCTGCCATTGCGAGAGGGCCAGTGGCCACCTATGGAGCAGCCTCAACGTC

AGTGGGGG 2600

CACCTCTGACCCTGCCCTCAACCACGTGGTCCAGCTGCTCACCTGTGACCTGCTACTGTCGCTACGGACAGCGCTCTGGCAAAAACAGGCCCA

GTGCCAGC 2700

CAGGCTGTGGGGGAGACCTACCACGCGTCAGGCGCTGAACTGGCGGGCTTCCAACGGGACCTGGGCAGCCTGCGCAGGCTGGCACACAGCT

TCCGCCCAG 2800

CATACCGCAAGGTGTTCCTGCATGAAGCCACCGTGCGCCTGATGGCAGGAGGCAGCCCCACCCGCACCCACCAGCTGCTGGAACACAGCCT

GCGGCGGCG 2900

CACCACGCAGAGCACCAAGCACGGAGAGGTGGATGCCTGGCCCGGCCAGCGAGAGCGGGCCACCGCCATCCTGCTGGCCTGCCGCCACCTG

CCCCTCTCC 3000

TTCCTCTCCTCCCCGGGCCAGCGGGCAGTGCTGCTGGCCGAAGCTGCCCGCACCCTGGAGAAGGTGGGCGACCGGCGCTCCTGCAACGACT

GCCAGCAGA 3100

TGATTGTTAAGCTGGGTGGTGGCACTGCCATTGCCGCCTCCTGACTCGAG 3150

TABLE 4

ISRP amino acid sequence (SEQ ID NO:6, from KpnI restriction site to XhoI restriction site, as described in Example 1). See also SEQ ID NO:4.

GTTMKPVTLYDVAEYAGVSYQTVSRVVNQASHVSAKTREKVEAAMAELNYIPNRVAQQLAGKQSLLIGVATSSLALHAPS

QIVAAIKSRADQLGASVVVSMVERSGVEACKAAVHNLLAQRVSGLIINYPLDDQDAIAVEAACTNVPALFLDVSDQTPIN

SIIFSHEDGTRLGVEHLVALGHQQIALLAGPLSSVSAKLRLAGWHKYLTKNQIQPIAEREGDWSAMSGFQQTMQMLNEGI

VPTAMLVANDQMALGAMRAITESGLRVGADISVVGYDDTEDSSCYIPPLTTIKQDFRLLGQTSVDRLLQLSQGQAVKGNQ

LLPVSLVKRKTTLAPNTQTASPRALADSLMQLARQVSRLESGQSSLRPPKKKRKVGSGALGMVDRSRILLCVLTFLCLSF

NPLTSLLQWGGAHDSDQHPHSGSGRSVLSFESGSGGWFDWMMPTLLLWLVNGVIVLSVFVKLLVHGEPVIRPHSRSSVTF

WRHRKQADLDLARGDFAAAAANLQTCLAVLGRALPTSRLDLACSLSWNVIRYSLQKLRLVRWLLKKVFQCRRATPATEAG

FEDEAKTSARDAALAYHRLHQLHITGKLPAGSACSDVHMALCAVNLAECAEEKIPPSTLVEIHLTAAMGLKTRCGGKLGF

LASYFLSRAQSLCGPEHSAVPDSLRWLCHPLGQKFFMERSWSVKSAAKESLYCAQRNPADPIAQVHQAFCKNLLERAIES

LVKPQAKKKAGDQEEESCEFSSALEYLKLLHSFVDSVGVMSPPLSRSSVLKSALGPDIICRWWTSAITVAISWLQGDDAA

VRSHFTKVERIPKALEVTESPLVKAIFHACRAMHASLPGKADGQQSSFCHCERASGHLWSSLNVSGGTSDPALNHVVQLL

TCDLLLSLRTALWQKQASASQAVGETYHASGAELAGFQRDLGSLRRLAHSFRPAYRKVFLHEATVRLMAGGSPTRTHQLL

TABLE 4-continued

ISRP amino acid sequence (SEQ ID NO:6, from KpnI restriction site to XhoI restriction site, as described in Example 1). See also SEQ ID NO:4.

EHSLRRRTTQSTKHGEVDAWPGQRERATAILLACRHLPLSFLSSPGQRAVLLAEAARTLEKVGDRKSCNDCQQMIVKLGG

GTAIAAS.LE

---

What is claimed is:

1. A method of evaluating a compound for the ability to inhibit proteolysis of a proteolytic substrate, comprising:
   (a) culturing a recombinant eukaryotic host cell which expresses (i) a chimeric protein comprising a transcription repressor portion and a protease recognition portion, said protease recognition portion comprising a proteolytic cleavage site of a proteolytic substrate of interest, wherein the chimeric polypeptide is attached to a non-nuclear membrane, and (ii) a reporter gene operably linked to a transcription regulatory sequence which is responsive to said transcription repressor;
   (b) adding a test compound to the recombinant host cell of step (a); and
   (c) monitoring expression of a reporter gene product, wherein an increase in expression in the presence of the test compound added in step (b) over expression in the absence of the test compound is an indication that the test compound inhibits proteolysis of the proteolytic substrate.

2. The method of claim 1, wherein the proteolytic substrate is a protein selected from the group consisting of an amyloid precursor protein, a sterol regulatory element binding protein, and a Notch receptor protein.

3. The method of claim 1, wherein the proteolytic substrate is an amyloid precursor protein.

4. The method of claim 1, wherein the proteolytic substrate is a sterol regulatory element binding protein.

5. The method of claim 4, wherein the sterol regulatory element binding protein (SREBP) is selected from the group consisting of SREBP-1a, SREBP-1c, and SREBP-2.

6. The method of claim 1, wherein the proteolytic substrate is a Notch receptor protein.

7. The method of claim 6, wherein the Notch receptor protein is selected from the group consisting of a Drosophila Notch protein, a *Caenorrhabditis elegans* LIN-12 protein, a *Caenorrhabditis elegans* GLP-1 protein, a murine Notch1 protein, and a murine Notch2 protein.

8. The method of claim 1, wherein the proteolysis is performed by a protease endogenous to said recombinant host cell.

9. The method of claim 8, wherein the protease is selected from the group consisting of β-secretase, γ-secretase, presenilin, SREBP cleavage activating protein (SCAP), Site-1 protease (S1P), and Site-2 protease (S2P).

10. The method of claim 1, wherein the proteae is a membrane-associated protease.

11. The method of claim 10, wherein the recombinant host cell is a mammalian cell, an insect cell, a yeast cell, an avian cell or an amphibian cell.

12. The method of claim 11, wherein the recombinant host cell is a mammalian cell.

13. The method of claim 12, wherein the mammalian cell is selected from the group consisting of CHO cells, COS-7 cells, Hep G2 cells, VERO cells, HeLa cells, human embryonic kidney cells, 293, W138 cells, BHK cells, MDCK cells, and monkey CV-1 cells.

14. The method of claim 1, wherein the transcription repressor portion of the chimeric protein is in polypeptide linkage to a nuclear localization signal.

15. The method of claim 1, wherein the transcription repressor is selected from the group consisting of a lacI repressor, a lambda CI repressor, a lambda cro repressor, a tet repressor, an araC repressor, a REST repressor and a Kox1 repressor.

16. The method of claim 1, wherein the reporter gene encodes a protein selected from the group consisting of luciferase, green fluorescent protein, red fluorescent protein, β-glucuronidase, chloramphenicol acetyltransferase, β-galactosidase, aqueorin, transferase, esterase, phosphatase, tissue plasminogen activator, and urokinase.

17. The method of claim 1, wherein the transcription regulatory sequence is selected from the group consisting of a lacI binding sequence, a lambda CI repressor binding sequence, a lambda cro repressor binding sequence, a tet repressor binding sequence, a araC repressor binding sequence, a REST repressor binding sequence and a Kox1 binding sequence.

18. A genetically modified cell comprising:
   (a) a first DNA sequence encoding a hybrid protein comprising a protease recognition site and a transcription repressor portion, wherein said hybrid protein is attached to a non-nuclear membrane; and
   (b) a second DNA sequence encoding a reporter protein, said second DNA sequence comprising a sequence encoding the reporter protein and a transcription regulatory sequence, said transcription regulatory sequence being operably linked to the sequence encoding the reporter protein.

19. The genetically modified cell of claim 18, wherein the modified host cell is a eukaryotic cell.

20. The genetically modified cell of claim 18, wherein the protease recognition site comprises a cleavage site of a protein selected from the group consisting of an amyloid precursor protein, a sterol regulatoiy element binding protein, and a Notch receptor protein.

21. The genetically modified cell of claim 20, wherein the protein is an amyloid precursor protein.

22. The genetically modified cell of claim 20, wherein the protein is a sterol regulatory element binding protein.

23. The genetically modified cell of claim 22, wherein said sterol regulatory element binding protein (SREBP) is selected from the group consisting of SREBP-1a, SREBP-1c, and SREBP-2.

24. The genetically modified cell of claim 20, wherein the protein is a Notch receptor protein.

25. The genetically modified cell of claim 24, wherein the Notch receptor protein is selected from the group consisfing of a Drosophila Notch protein, a *Caenorrhabitis elegans* LIN-12 protein, a *Caenorrhabditis elegans* GLP-1 protein, a murine Notch1 protein, and a murine Notch2 protein.

26. The genetically modified cell of claim 20, wherein the modified host cell is a mammalian cell.

27. The genetically modified cell of claim 19, wherein the mammalian cell is selected from the group consisting of CHO cells, COS-7 cells, Hep G2 cells, VERO cells, HeLa cells, human embryonic kidney cells, 293, W138 cells, BHK cells, MDCK cells, and monkey CV-1 cells.

28. The genetically modified cell of claim 19, wherein the transcription repressor is selected from the group consisting of a lacI repressor, a lambda CI repressor, a lambda cro repressor, a tet repressor, an araC repressor, a REST repressor and a Kox1 repressor.

29. The genetically modified cell of claim 19, wherein the reporter gene is selected from the group consisting of luciferase, green fluorescent protein, red fluorescent protein, chloramphenicol acetyltransferase (CAT), a transferae, aequorin, an esterase, a phosphatase, tissue plasminogen activator, and urokinase.

30. The genetically modified cell of claim 19, wherein the transcription regulatory sequence is selected from the group consisting of a lacI binding sequence, a lambda CI repressor binding sequence, a lambda cro repressor binding sequence, a tet repressor binding sequence, a araC repressor binding sequence, a REST repressor binding sequence and a Kox1 binding sequence.

31. A method for identifying compounds which inhibit proteolysis of a proteolytic substrate, comprising:
 (a) administering a test compound to the genetically modified cell of claim 20 and incubating the modified host cell for a suitable period;
 (b) determining whether the administration of the compound increases expression of the reporter gene; and
 (c) identifying a test compound which increases expression of the reporter gene as an inhibitor of proteolysis of said proteolytic substrate.

32. A DNA construct comprising a nucleotide sequence encoding a fusion protein, said fusion protein comprising a transcription repressor portion and a proteolytic cleavage recognition portion and a membrane targeting portion, wherein said nucleotide sequence is operably linked to trascription regulatory signals.

33. The DNA construct of claim 32 wherein the fusion protein further comprises a nuclear localization signal portion in peptide linkage with the transcription repressor portion.

34. The DNA construct of claim 32 wherein the transcription repressor portion is a lacI repressor portion having transcription repressing activity when associated with a lacO DNA sequence.

35. The DNA construct of claim 32 wherein the proteolytic cleavage recognition portion is from an amyloid precursor protein.

36. The DNA construct of claim 34 wherein the fusion protein has the amino acid sequence of SEQ ID NO:2.

37. The DNA construt of claim 36 wherein the nucleotide sequence encoding the fusion protein is the nucleotide sequence of SEQ ID NO:1, nucleotides 12–3083.

38. The DNA construct of claim 37 which is pCMV-APPI.

39. The DNA construct of claim 32 wherein the proteolytic cleavage recognition portion is from a Notch protein.

40. The DNA construct of claim 39 wherein the fusion protein has the amino acid sequence of SEQ ID NO:4.

41. The DNA construct of claim 40 wherein the nucleotide sequence encoding the fusion protein is the nucleotide scquence as given in SEQ ID NO:3, nucleotides 12–1334.

42. The DNA ronstruct of claim 41 which is pCMV-NotI.

43. The DNA construct of claim 32 wherein the proteolytic cleavage recognition portion is from a sterol responsive element binding protein.

44. The DNA construct of claim 43 wherein the proteolytic cleavage recognition portion is from sterol responsive element binding protein 2.

45. The DNA construct of claim 44 wherein the fusion protein comprises the amino acid sequence of SEQ ID NO:6.

46. The DNA construct of claim 45 wherein the nucleotide sequence encoding the fusion protein comprises the nucleotide sequence as given in SEQ ID NO:5.

47. The DNA construct of claim 46 which is pCMV-ISRP.

48. A genetically modified cell comprising a DNA construct selected from the group consisting of pCMV-APPI, pCMV-NotI, pTMI, pTMI-C3, and pCMV-ISRP.

* * * * *

SEQUENCE LISTING

<160> NUMBER OF SEQ ID NOS: 32

<210> SEQ ID NO 1
<211> LENGTH: 3092
<212> TYPE: DNA
<213> ORGANISM: Artificial Sequence
<220> FEATURE:
<223> OTHER INFORMATION: Description of Artificial Sequence:contains
      APP-LacI fusion protein
<220> FEATURE:
<221> NAME/KEY: CDS
<222> LOCATION: (12)..(3083)

<400> SEQUENCE: 1

```
aagcttccac c atg ctg ccc ggt ttg gca ctg ctc ctg ctg gcc gcc tgg         50
            Met Leu Pro Gly Leu Ala Leu Leu Leu Leu Ala Ala Trp
              1               5                  10 acg gct cgg gcg ctg gag gta ccc act gat ggt aat gct ggc ctg ctg          98
Thr Ala Arg Ala Leu Glu Val Pro Thr Asp Gly Asn Ala Gly Leu Leu
 15                  20                  25 gct gaa ccc cag att gcc atg ttc tgt ggc aga ctg aac atg cac atg         146
Ala Glu Pro Gln Ile Ala Met Phe Cys Gly Arg Leu Asn Met His Met
 30                  35                  40                  45 aat gtc cag aat ggg aag tgg gat tca gat cca tca ggg acc aaa acc         194
Asn Val Gln Asn Gly Lys Trp Asp Ser Asp Pro Ser Gly Thr Lys Thr
                 50                  55                  60 tgc att gat acc aag gaa ggc atc ctg cag tat tgc caa gaa gtc tac         242
Cys Ile Asp Thr Lys Glu Gly Ile Leu Gln Tyr Cys Gln Glu Val Tyr
             65                  70                  75 cct gaa ctg cag atc acc aat gtg gta gaa gcc aac caa cca gtg acc         290
Pro Glu Leu Gln Ile Thr Asn Val Val Glu Ala Asn Gln Pro Val Thr
         80                  85                  90 atc cag aac tgg tgc aag cgg ggc cgc aag cag tgc aag acc cat ccc         338
Ile Gln Asn Trp Cys Lys Arg Gly Arg Lys Gln Cys Lys Thr His Pro
     95                 100                 105 cac ttt gtg att ccc tac cgc tgc tta gtt ggt gag ttt gta agt gat         386
His Phe Val Ile Pro Tyr Arg Cys Leu Val Gly Glu Phe Val Ser Asp
110                 115                 120                 125 gcc ctt ctc gtt cct gac aag tgc aaa ttc tta cac cag gag agg atg         434
Ala Leu Leu Val Pro Asp Lys Cys Lys Phe Leu His Gln Glu Arg Met
                130                 135                 140 gat gtt tgc gaa act cat ctt cac tgg cac acc gtc gcc aaa gag aca         482
Asp Val Cys Glu Thr His Leu His Trp His Thr Val Ala Lys Glu Thr
            145                 150                 155 tgc agt gag aag agt acc aac ttg cat gac tac ggc atg ttg ctg ccc         530
Cys Ser Glu Lys Ser Thr Asn Leu His Asp Tyr Gly Met Leu Leu Pro
        160                 165                 170 tgc gga att gac aag ttc cga ggg gta gag ttt gtg tgt tgc cca ctg         578
Cys Gly Ile Asp Lys Phe Arg Gly Val Glu Phe Val Cys Cys Pro Leu
    175                 180                 185
```

```
gct gaa gaa agt gac aat gtg gat tct gct gat gcg gag gag gat gac       626
Ala Glu Glu Ser Asp Asn Val Asp Ser Ala Asp Ala Glu Glu Asp Asp
190                 195                 200                 205 tcg gat gtc tgg tgg ggc gga gca gac aca gac tat gca gat ggg agt       674
Ser Asp Val Trp Trp Gly Gly Ala Asp Thr Asp Tyr Ala Asp Gly Ser
                210                 215                 220 gaa gac aaa gta gta gaa gta gca gag gag gaa gaa gtg gct gag gtg       722
Glu Asp Lys Val Val Glu Val Ala Glu Glu Glu Glu Val Ala Glu Val
            225                 230                 235 gaa gaa gaa gaa gcc gat gat gac gag gac gat gag gat ggt gat gag       770
Glu Glu Glu Glu Ala Asp Asp Asp Glu Asp Asp Glu Asp Gly Asp Glu
        240                 245                 250 gta gag gaa gag gct gag gaa ccc tac gaa gaa gcc aca gag aga acc       818
Val Glu Glu Glu Ala Glu Glu Pro Tyr Glu Glu Ala Thr Glu Arg Thr
255                 260                 265 acc agc att gcc acc acc acc acc acc aca gag tct gtg gaa gag           866
Thr Ser Ile Ala Thr Thr Thr Thr Thr Thr Glu Ser Val Glu Glu
270                 275                 280                 285 gtg gtt cga gtt cct aca aca gca gcc agt acc cct gat gcc gtt gac       914
Val Val Arg Val Pro Thr Thr Ala Ala Ser Thr Pro Asp Ala Val Asp
                290                 295                 300 aag tat ctc gag aca cct ggg gat gag aat gaa cat gcc cat ttc cag       962
Lys Tyr Leu Glu Thr Pro Gly Asp Glu Asn Glu His Ala His Phe Gln
            305                 310                 315 aaa gcc aaa gag agg ctt gag gcc aag cac cga gag aga atg tcc cag      1010
Lys Ala Lys Glu Arg Leu Glu Ala Lys His Arg Glu Arg Met Ser Gln
        320                 325                 330 gtc atg aga gaa tgg gaa gag gca gaa cgt caa gca aag aac ttg cct      1058
Val Met Arg Glu Trp Glu Glu Ala Glu Arg Gln Ala Lys Asn Leu Pro
335                 340                 345 aaa gct gat aag aag gca gtt atc cag cat ttc cag gag aaa gtg gaa      1106
Lys Ala Asp Lys Lys Ala Val Ile Gln His Phe Gln Glu Lys Val Glu
350                 355                 360                 365 tct ttg gaa cag gaa gca gcc aac gag aga cag cag ctg gtg gag aca      1154
Ser Leu Glu Gln Glu Ala Ala Asn Glu Arg Gln Gln Leu Val Glu Thr
                370                 375                 380 cac atg gcc aga gtg gaa gcc atg ctc aat gac cgc cgc cgc ctg gcc      1202
His Met Ala Arg Val Glu Ala Met Leu Asn Asp Arg Arg Arg Leu Ala
            385                 390                 395 ctg gag aac tac atc acc gct ctg cag gct gtt cct cct cgg cct cgt      1250
Leu Glu Asn Tyr Ile Thr Ala Leu Gln Ala Val Pro Pro Arg Pro Arg
        400                 405                 410 cac gtg ttc aat atg cta aag aag tat gtc cgc gca gaa cag aag gac      1298
His Val Phe Asn Met Leu Lys Lys Tyr Val Arg Ala Glu Gln Lys Asp
415                 420                 425 aga cag cac acc cta aag cat ttc gag cat gtg cgc atg gtg gat ccc      1346
Arg Gln His Thr Leu Lys His Phe Glu His Val Arg Met Val Asp Pro
430                 435                 440                 445 aag aaa gcc gct cag atc cgg tcc cag gtt atg aca cac ctc cgt gtg      1394
Lys Lys Ala Ala Gln Ile Arg Ser Gln Val Met Thr His Leu Arg Val
                450                 455                 460 att tat gag cgc atg aat cag tct ctc tcc ctg ctc tac aac gtg cct      1442
Ile Tyr Glu Arg Met Asn Gln Ser Leu Ser Leu Leu Tyr Asn Val Pro
            465                 470                 475 gca gtg gcc gag gag att cag gat gaa gtt gat gag ctg ctt cag aaa      1490
Ala Val Ala Glu Glu Ile Gln Asp Glu Val Asp Glu Leu Leu Gln Lys
        480                 485                 490 gag caa aac tat tca gat gac gtc ttg gcc aac atg att agt gaa cca      1538
Glu Gln Asn Tyr Ser Asp Asp Val Leu Ala Asn Met Ile Ser Glu Pro
495                 500                 505
```

| | | |
|---|---|---|
| agg atc agt tac gga aac gat gct ctc atg cca tct ttg acc gaa acg<br>Arg Ile Ser Tyr Gly Asn Asp Ala Leu Met Pro Ser Leu Thr Glu Thr<br>510                            515                         520                       525 | 1586 |
| aaa acc acc gtg gag ctc ctt ccc gtg aat gga gag ttc agc ctg gac<br>Lys Thr Thr Val Glu Leu Leu Pro Val Asn Gly Glu Phe Ser Leu Asp<br>                         530                         535                       540 | 1634 |
| gat ctc cag ccg tgg cat tct ttt ggg gct gac tct gtg cca gcc aac<br>Asp Leu Gln Pro Trp His Ser Phe Gly Ala Asp Ser Val Pro Ala Asn<br>                  545                       550                       555 | 1682 |
| aca gaa aac gaa gtt gag cct gtt gat gcc cgc cct gct gcc gac cga<br>Thr Glu Asn Glu Val Glu Pro Val Asp Ala Arg Pro Ala Ala Asp Arg<br>      560                       565                       570 | 1730 |
| gga ctg acc act cga cca ggt tct ggg ttg aca aat atc aag acg gag<br>Gly Leu Thr Thr Arg Pro Gly Ser Gly Leu Thr Asn Ile Lys Thr Glu<br>575                         580                         585 | 1778 |
| gag atc tct gaa gtg aag atg gat gca gaa ttc cga cat gac tca gga<br>Glu Ile Ser Glu Val Lys Met Asp Ala Glu Phe Arg His Asp Ser Gly<br>590                         595                       600                       605 | 1826 |
| tat gaa gtt cat cat caa aaa ttg gtg ttc ttt gca gaa gat gtg ggt<br>Tyr Glu Val His His Gln Lys Leu Val Phe Phe Ala Glu Asp Val Gly<br>                  610                       615                       620 | 1874 |
| tca aac aaa ggt gca atc att gga ctc atg gtg ggc ggt gtt gtc ata<br>Ser Asn Lys Gly Ala Ile Ile Gly Leu Met Val Gly Gly Val Val Ile<br>              625                       630                       635 | 1922 |
| gcg aca gtg atc gtc atc acc ttg gtg atg ctg aag aag aaa gga tcc<br>Ala Thr Val Ile Val Ile Thr Leu Val Met Leu Lys Lys Lys Gly Ser<br>640                         645                       650 | 1970 |
| gga cca gta acg tta tac gat gtc gca gag tat gcc ggt gtc tct tat<br>Gly Pro Val Thr Leu Tyr Asp Val Ala Glu Tyr Ala Gly Val Ser Tyr<br>655                         660                       665 | 2018 |
| cag acc gtt tcc cgc gtg gtg aac cag gcc agc cac gtt tct gcg aaa<br>Gln Thr Val Ser Arg Val Val Asn Gln Ala Ser His Val Ser Ala Lys<br>670                         675                       680                       685 | 2066 |
| acg cgg gaa aaa gtg gaa gcg gcg atg gcg gag ctg aat tac att ccc<br>Thr Arg Glu Lys Val Glu Ala Ala Met Ala Glu Leu Asn Tyr Ile Pro<br>                         690                       695                       700 | 2114 |
| aac cgc gtg gca caa caa ctg gcg ggc aaa cag tcg ttg ctg att ggc<br>Asn Arg Val Ala Gln Gln Leu Ala Gly Lys Gln Ser Leu Leu Ile Gly<br>                  705                       710                       715 | 2162 |
| gtt gcc acc tcc agt ctg gcc ctg cac gcg ccg tcg caa att gtc gcg<br>Val Ala Thr Ser Ser Leu Ala Leu His Ala Pro Ser Gln Ile Val Ala<br>720                         725                       730 | 2210 |
| gcg att aaa tct cgc gcc gat caa ctg ggt gcc agc gtg gtg gtg tcg<br>Ala Ile Lys Ser Arg Ala Asp Gln Leu Gly Ala Ser Val Val Val Ser<br>735                         740                       745 | 2258 |
| atg gta gaa cga agc ggc gtc gaa gcc tgt aaa gcg gcg gtg cac aat<br>Met Val Glu Arg Ser Gly Val Glu Ala Cys Lys Ala Ala Val His Asn<br>750                         755                       760                       765 | 2306 |
| ctt ctc gcg caa cgc gtc agt ggg ctg atc att aac tat ccg ctg gat<br>Leu Leu Ala Gln Arg Val Ser Gly Leu Ile Ile Asn Tyr Pro Leu Asp<br>                         770                       775                       780 | 2354 |
| gac cag gat gcc att gct gtg gaa gct gcc tgc act aat gtt ccg gcg<br>Asp Gln Asp Ala Ile Ala Val Glu Ala Ala Cys Thr Asn Val Pro Ala<br>                  785                       790                       795 | 2402 |
| tta ttt ctt gat gtc tct gac cag aca ccc atc aac agt att att ttc<br>Leu Phe Leu Asp Val Ser Asp Gln Thr Pro Ile Asn Ser Ile Ile Phe<br>                  800                       805                       810 | 2450 |
| tcc cat gaa gac ggt acg cga ctg ggc gtg gag cat ctg gtc gca ttg<br>Ser His Glu Asp Gly Thr Arg Leu Gly Val Glu His Leu Val Ala Leu<br>        815                       820                       825 | 2498 |

-continued

```
ggt cac cag caa atc gcg ctg tta gcg ggc cca tta agt tct gtc tcg       2546
Gly His Gln Gln Ile Ala Leu Leu Ala Gly Pro Leu Ser Ser Val Ser
830                 835                 840                 845 gcg cgt ctg cgt ctg gct ggc tgg cat aaa tat ctc act cgc aat caa       2594
Ala Arg Leu Arg Leu Ala Gly Trp His Lys Tyr Leu Thr Arg Asn Gln
                850                 855                 860 att cag ccg ata gcg gaa cgg gaa ggc gac tgg agt gcc atg tcc ggt       2642
Ile Gln Pro Ile Ala Glu Arg Glu Gly Asp Trp Ser Ala Met Ser Gly
            865                 870                 875 ttt caa caa acc atg caa atg ctg aat gag ggc atc gtt ccc act gcg       2690
Phe Gln Gln Thr Met Gln Met Leu Asn Glu Gly Ile Val Pro Thr Ala
        880                 885                 890 atg ctg gtt gcc aac gat cag atg gcg ctg ggc gca atg cgc gcc att       2738
Met Leu Val Ala Asn Asp Gln Met Ala Leu Gly Ala Met Arg Ala Ile
    895                 900                 905 acc gag tcc ggg ctg cgc gtt ggt gcg gat atc tcg gta gtg gga tac       2786
Thr Glu Ser Gly Leu Arg Val Gly Ala Asp Ile Ser Val Val Gly Tyr
910                 915                 920                 925 gac gat acc gaa gac agc tca tgt tat atc ccg ccg tta acc acc atc       2834
Asp Asp Thr Glu Asp Ser Ser Cys Tyr Ile Pro Pro Leu Thr Thr Ile
                930                 935                 940 aaa cag gat ttt cgc ctg ctg ggg caa acc agc gtg gac cgc ttg ctg       2882
Lys Gln Asp Phe Arg Leu Leu Gly Gln Thr Ser Val Asp Arg Leu Leu
            945                 950                 955 caa ctc tct cag ggc cag gcg gtg aag ggc aat cag ctg ttg ccc gtc       2930
Gln Leu Ser Gln Gly Gln Ala Val Lys Gly Asn Gln Leu Leu Pro Val
        960                 965                 970 tca ctg gtg aaa aga aaa acc acc ctg gcg ccc aat acg caa acc gcc       2978
Ser Leu Val Lys Arg Lys Thr Thr Leu Ala Pro Asn Thr Gln Thr Ala
    975                 980                 985 tct ccc cgc gcg ttg gcc gat tca tta atg cag ctg gca cga cag gtt       3026
Ser Pro Arg Ala Leu Ala Asp Ser Leu Met Gln Leu Ala Arg Gln Val
990                 995                 1000                1005 tcc cga ctg gaa agc ggg cag agc agc ctg agg cct cct aag aag aag       3074
Ser Arg Leu Glu Ser Gly Gln Ser Ser Leu Arg Pro Pro Lys Lys Lys
                1010                1015                1020 agg aag gtt tgatctaga                                                 3092
Arg Lys Val <210> SEQ ID NO 2
<211> LENGTH: 1024
<212> TYPE: PRT
<213> ORGANISM: Artificial Sequence
<220> FEATURE:
<223> OTHER INFORMATION: Description of Artificial Sequence:contains
      APP-LacI fusion protein

<400> SEQUENCE: 2

Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
    65                  70                  75                  80

Gln Ile Thr Asn Val Val Glu Ala Asn Gln Pro Val Thr Ile Gln Asn
                85                  90                  95
```

-continued

```
Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
                180                 185                 190

Ser Asp Asn Val Asp Ser Ala Asp Ala Glu Glu Asp Asp Ser Asp Val
                195                 200                 205

Trp Trp Gly Gly Ala Asp Thr Asp Tyr Ala Asp Gly Ser Glu Asp Lys
            210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Val Pro Thr Thr Ala Ala Ser Thr Pro Asp Ala Val Asp Lys Tyr Leu
            290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
                340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
            370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
            450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510
```

-continued

```
Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
            530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
                595                 600                 605

His His Gln Lys Leu Val Phe Phe Ala Glu Asp Val Gly Ser Asn Lys
        610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gly Ser Gly Pro Val
                645                 650                 655

Thr Leu Tyr Asp Val Ala Glu Tyr Ala Gly Val Ser Tyr Gln Thr Val
            660                 665                 670

Ser Arg Val Val Asn Gln Ala Ser His Val Ser Ala Lys Thr Arg Glu
                675                 680                 685

Lys Val Glu Ala Ala Met Ala Glu Leu Asn Tyr Ile Pro Asn Arg Val
        690                 695                 700

Ala Gln Gln Leu Ala Gly Lys Gln Ser Leu Leu Ile Gly Val Ala Thr
705                 710                 715                 720

Ser Ser Leu Ala Leu His Ala Pro Ser Gln Ile Val Ala Ala Ile Lys
            725                 730                 735

Ser Arg Ala Asp Gln Leu Gly Ala Ser Val Val Val Ser Met Val Glu
            740                 745                 750

Arg Ser Gly Val Glu Ala Cys Lys Ala Ala Val His Asn Leu Leu Ala
        755                 760                 765

Gln Arg Val Ser Gly Leu Ile Ile Asn Tyr Pro Leu Asp Asp Gln Asp
        770                 775                 780

Ala Ile Ala Val Glu Ala Ala Cys Thr Asn Val Pro Ala Leu Phe Leu
785                 790                 795                 800

Asp Val Ser Asp Gln Thr Pro Ile Asn Ser Ile Ile Phe Ser His Glu
                805                 810                 815

Asp Gly Thr Arg Leu Gly Val Glu His Leu Val Ala Leu Gly His Gln
            820                 825                 830

Gln Ile Ala Leu Leu Ala Gly Pro Leu Ser Ser Val Ser Ala Arg Leu
        835                 840                 845

Arg Leu Ala Gly Trp His Lys Tyr Leu Thr Arg Asn Gln Ile Gln Pro
    850                 855                 860

Ile Ala Glu Arg Glu Gly Asp Trp Ser Ala Met Ser Gly Phe Gln Gln
865                 870                 875                 880

Thr Met Gln Met Leu Asn Glu Gly Ile Val Pro Thr Ala Met Leu Val
                885                 890                 895

Ala Asn Asp Gln Met Ala Leu Gly Ala Met Arg Ala Ile Thr Glu Ser
            900                 905                 910

Gly Leu Arg Val Gly Ala Asp Ile Ser Val Val Gly Tyr Asp Asp Thr
        915                 920                 925
```

```
Glu Asp Ser Ser Cys Tyr Ile Pro Pro Leu Thr Thr Ile Lys Gln Asp
    930                 935                 940

Phe Arg Leu Leu Gly Gln Thr Ser Val Asp Arg Leu Leu Gln Leu Ser
945                 950                 955                 960

Gln Gly Gln Ala Val Lys Gly Asn Gln Leu Leu Pro Val Ser Leu Val
                965                 970                 975

Lys Arg Lys Thr Thr Leu Ala Pro Asn Thr Gln Thr Ala Ser Pro Arg
            980                 985                 990

Ala Leu Ala Asp Ser Leu Met Gln Leu Ala Arg Gln Val Ser Arg Leu
        995                1000                1005

Glu Ser Gly Gln Ser Ser Leu Arg Pro Pro Lys Lys Arg Lys Val
   1010                1015                1020
```

<210> SEQ ID NO 3
<211> LENGTH: 1341
<212> TYPE: DNA
<213> ORGANISM: Artificial Sequence
<220> FEATURE:
<223> OTHER INFORMATION: Description of Artificial Sequence:Contains
      sequence encoding NotchI-LacI Fusion Protein
<220> FEATURE:
<221> NAME/KEY: CDS
<222> LOCATION: (12)..(1334)

<400> SEQUENCE: 3

```
aagcttccac c atg cca cgg ctc ctg acg ccc ctt ctc tgc cta acg ctg         50
            Met Pro Arg Leu Leu Thr Pro Leu Leu Cys Leu Thr Leu
             1               5                  10 ctg ccc gcg cgc gcc gca aga ggc att ccc tac aag atc gaa gcc gta         98
Leu Pro Ala Arg Ala Ala Arg Gly Ile Pro Tyr Lys Ile Glu Ala Val
 15                  20                  25 aag agt gag acg gtg gag cct ccg ctg ccc tca cag ctg cac ctc atg        146
Lys Ser Glu Thr Val Glu Pro Pro Leu Pro Ser Gln Leu His Leu Met
 30                  35                  40                  45 tac gtg gcg gca gct gcc ttc gtg ctc ctg ttc ttt gtg ggc tgt ggg        194
Tyr Val Ala Ala Ala Ala Phe Val Leu Leu Phe Phe Val Gly Cys Gly
                 50                  55                  60 gtg ctg ctg tcc cgc aag cgc gga tcc gga cca gta acg tta tac gat        242
Val Leu Leu Ser Arg Lys Arg Gly Ser Gly Pro Val Thr Leu Tyr Asp
             65                  70                  75 gtc gca gag tat gcc ggt gtc tct tat cag acc gtt tcc cgc gtg gtg        290
Val Ala Glu Tyr Ala Gly Val Ser Tyr Gln Thr Val Ser Arg Val Val
         80                  85                  90 aac cag gcc agc cac gtt tct gcg aaa acg cgg gaa aaa gtg gaa gcg        338
Asn Gln Ala Ser His Val Ser Ala Lys Thr Arg Glu Lys Val Glu Ala
     95                 100                 105 gcg atg gcg gag ctg aat tac att ccc aac cgc gtg gca caa caa ctg        386
Ala Met Ala Glu Leu Asn Tyr Ile Pro Asn Arg Val Ala Gln Gln Leu
110                 115                 120                 125 gcg ggc aaa cag tcg ttg ctg att ggc gtt gcc acc tcc agt ctg gcc        434
Ala Gly Lys Gln Ser Leu Leu Ile Gly Val Ala Thr Ser Ser Leu Ala
                130                 135                 140 ctg cac gcg ccg tcg caa att gtc gcg gcg att aaa tct cgc gcc gat        482
Leu His Ala Pro Ser Gln Ile Val Ala Ala Ile Lys Ser Arg Ala Asp
            145                 150                 155 caa ctg ggt gcc agc gtg gtg gtg tcg atg gta gaa cga agc ggc gtc        530
Gln Leu Gly Ala Ser Val Val Val Ser Met Val Glu Arg Ser Gly Val
        160                 165                 170 gaa gcc tgt aaa gcg gcg gtg cac aat ctt ctc gcg caa cgc gtc agt        578
Glu Ala Cys Lys Ala Ala Val His Asn Leu Leu Ala Gln Arg Val Ser
    175                 180                 185
```

-continued

```
ggg ctg atc att aac tat ccg ctg gat gac cag gat gcc att gct gtg         626
Gly Leu Ile Ile Asn Tyr Pro Leu Asp Asp Gln Asp Ala Ile Ala Val
190                 195                 200                 205 gaa gct gcc tgc act aat gtt ccg gcg tta ttt ctt gat gtc tct gac         674
Glu Ala Ala Cys Thr Asn Val Pro Ala Leu Phe Leu Asp Val Ser Asp
                210                 215                 220 cag aca ccc atc aac agt att att ttc tcc cat gaa gac ggt acg cga         722
Gln Thr Pro Ile Asn Ser Ile Ile Phe Ser His Glu Asp Gly Thr Arg
            225                 230                 235 ctg ggc gtg gag cat ctg gtc gca ttg ggt cac cag caa atc gcg ctg         770
Leu Gly Val Glu His Leu Val Ala Leu Gly His Gln Gln Ile Ala Leu
        240                 245                 250 tta gcg ggc cca tta agt tct gtc tcg gcg cgt ctg cgt ctg gct ggc         818
Leu Ala Gly Pro Leu Ser Ser Val Ser Ala Arg Leu Arg Leu Ala Gly
    255                 260                 265 tgg cat aaa tat ctc act cgc aat caa att cag ccg ata gcg gaa cgg         866
Trp His Lys Tyr Leu Thr Arg Asn Gln Ile Gln Pro Ile Ala Glu Arg
270                 275                 280                 285 gaa ggc gac tgg agt gcc atg tcc ggt ttt caa caa acc atg caa atg         914
Glu Gly Asp Trp Ser Ala Met Ser Gly Phe Gln Gln Thr Met Gln Met
                290                 295                 300 ctg aat gag ggc atc gtt ccc act gcg atg ctg gtt gcc aac gat cag         962
Leu Asn Glu Gly Ile Val Pro Thr Ala Met Leu Val Ala Asn Asp Gln
            305                 310                 315 atg gcg ctg ggc gca atg cgc gcc att acc gag tcc ggg ctg cgc gtt        1010
Met Ala Leu Gly Ala Met Arg Ala Ile Thr Glu Ser Gly Leu Arg Val
        320                 325                 330 ggt gcg gat atc tcg gta gtg gga tac gac gat acc gaa gac agc tca        1058
Gly Ala Asp Ile Ser Val Val Gly Tyr Asp Asp Thr Glu Asp Ser Ser
    335                 340                 345 tgt tat atc ccg ccg tta acc acc atc aaa cag gat ttt cgc ctg ctg        1106
Cys Tyr Ile Pro Pro Leu Thr Thr Ile Lys Gln Asp Phe Arg Leu Leu
350                 355                 360                 365 ggg caa acc agc gtg gac cgc ttg ctg caa ctc tct cag ggc cag gcg        1154
Gly Gln Thr Ser Val Asp Arg Leu Leu Gln Leu Ser Gln Gly Gln Ala
                370                 375                 380 gtg aag ggc aat cag ctg ttg ccc gtc tca ctg gtg aaa aga aaa acc        1202
Val Lys Gly Asn Gln Leu Leu Pro Val Ser Leu Val Lys Arg Lys Thr
            385                 390                 395 acc ctg gcg ccc aat acg caa acc gcc tct ccc cgc gcg ttg gcc gat        1250
Thr Leu Ala Pro Asn Thr Gln Thr Ala Ser Pro Arg Ala Leu Ala Asp
        400                 405                 410 tca tta atg cag ctg gca cga cag gtt tcc cga ctg gaa agc ggg cag        1298
Ser Leu Met Gln Leu Ala Arg Gln Val Ser Arg Leu Glu Ser Gly Gln
    415                 420                 425 agc agc ctg agg cct cct aag aag aag agg aag gtt tgatcta                1341
Ser Ser Leu Arg Pro Pro Lys Lys Lys Arg Lys Val
430                 435                 440
```

<210> SEQ ID NO 4
<211> LENGTH: 441
<212> TYPE: PRT
<213> ORGANISM: Artificial Sequence
<220> FEATURE:
<223> OTHER INFORMATION: Description of Artificial Sequence:Contains
      sequence encoding NotchI-LacI Fusion Protein

<400> SEQUENCE: 4

Met Pro Arg Leu Leu Thr Pro Leu Leu Cys Leu Thr Leu Leu Pro Ala
1               5                   10                  15

-continued

```
Arg Ala Ala Arg Gly Ile Pro Tyr Lys Ile Glu Ala Val Lys Ser Glu
             20                  25                  30

Thr Val Glu Pro Pro Leu Pro Ser Gln Leu His Leu Met Tyr Val Ala
         35                  40                  45

Ala Ala Ala Phe Val Leu Leu Phe Phe Val Gly Cys Gly Val Leu Leu
     50                  55                  60

Ser Arg Lys Arg Gly Ser Gly Pro Val Thr Leu Tyr Asp Val Ala Glu
 65                  70                  75                  80

Tyr Ala Gly Val Ser Tyr Gln Thr Val Ser Arg Val Val Asn Gln Ala
                 85                  90                  95

Ser His Val Ser Ala Lys Thr Arg Glu Lys Val Glu Ala Ala Met Ala
             100                 105                 110

Glu Leu Asn Tyr Ile Pro Asn Arg Val Ala Gln Gln Leu Ala Gly Lys
         115                 120                 125

Gln Ser Leu Leu Ile Gly Val Ala Thr Ser Ser Leu Ala Leu His Ala
     130                 135                 140

Pro Ser Gln Ile Val Ala Ala Ile Lys Ser Arg Ala Asp Gln Leu Gly
145                 150                 155                 160

Ala Ser Val Val Val Ser Met Val Glu Arg Ser Gly Val Glu Ala Cys
                 165                 170                 175

Lys Ala Val His Asn Leu Leu Ala Gln Arg Val Ser Gly Leu Ile
             180                 185                 190

Ile Asn Tyr Pro Leu Asp Asp Gln Asp Ala Ile Ala Val Glu Ala Ala
         195                 200                 205

Cys Thr Asn Val Pro Ala Leu Phe Leu Asp Val Ser Asp Gln Thr Pro
     210                 215                 220

Ile Asn Ser Ile Ile Phe Ser His Glu Asp Gly Thr Arg Leu Gly Val
225                 230                 235                 240

Glu His Leu Val Ala Leu Gly His Gln Gln Ile Ala Leu Leu Ala Gly
                 245                 250                 255

Pro Leu Ser Ser Val Ser Ala Arg Leu Arg Leu Ala Gly Trp His Lys
             260                 265                 270

Tyr Leu Thr Arg Asn Gln Ile Gln Pro Ile Ala Glu Arg Glu Gly Asp
         275                 280                 285

Trp Ser Ala Met Ser Gly Phe Gln Gln Thr Met Gln Met Leu Asn Glu
     290                 295                 300

Gly Ile Val Pro Thr Ala Met Leu Val Ala Asn Asp Gln Met Ala Leu
305                 310                 315                 320

Gly Ala Met Arg Ala Ile Thr Glu Ser Gly Leu Arg Val Gly Ala Asp
                 325                 330                 335

Ile Ser Val Val Gly Tyr Asp Asp Thr Glu Asp Ser Ser Cys Tyr Ile
             340                 345                 350

Pro Pro Leu Thr Thr Ile Lys Gln Asp Phe Arg Leu Leu Gly Gln Thr
         355                 360                 365

Ser Val Asp Arg Leu Leu Gln Leu Ser Gln Gly Gln Ala Val Lys Gly
     370                 375                 380

Asn Gln Leu Leu Pro Val Ser Leu Val Lys Arg Lys Thr Thr Leu Ala
385                 390                 395                 400

Pro Asn Thr Gln Thr Ala Ser Pro Arg Ala Leu Ala Asp Ser Leu Met
                 405                 410                 415
```

Gln Leu Ala Arg Gln Val Ser Arg Leu Glu Ser Gly Gln Ser Ser Leu
            420                 425                 430

Arg Pro Pro Lys Lys Arg Lys Val
            435                 440

<210> SEQ ID NO 5
<211> LENGTH: 3150
<212> TYPE: DNA
<213> ORGANISM: Artificial Sequence
<220> FEATURE:
<223> OTHER INFORMATION: Description of Artificial Sequence:Contains
      partial sequence  encoding SREBP-LacI Fusion
      Protein from KpnI to XhoI.

<400> SEQUENCE: 5

| | | | | | |
|---|---|---|---|---|---|
| ggtaccacca | tgaaaccagt | aacgttatac | gatgtcgcag | agtatgccgg | tgtctcttat | 60 |
| cagaccgttt | cccgcgtggt | gaaccaggcc | agccacgttt | ctgcgaaaac | gcgggaaaaa | 120 |
| gtggaagcgg | cgatggcgga | gctgaattac | attcccaacc | gcgtggcaca | caactggcg | 180 |
| ggcaaacagt | cgttgctgat | tggcgttgcc | acctccagtc | tggccctgca | cgcgccgtcg | 240 |
| caaattgtcg | cggcgattaa | atctcgcgcc | gatcaactgg | gtgccagcgt | ggtggtgtcg | 300 |
| atggtagaac | gaagcggcgt | cgaagcctgt | aaagcggcgg | tgcacaatct | tctcgcgcaa | 360 |
| cgcgtcagtg | ggctgatcat | taactatccg | ctggatgacc | aggatgccat | tgctgtggaa | 420 |
| gctgcctgca | ctaatgttcc | ggcgttattt | cttgatgtct | ctgaccagac | acccatcaac | 480 |
| agtattattt | tctcccatga | agacggtacg | cgactgggcg | tggagcatct | ggtcgcattg | 540 |
| ggtcaccagc | aaatcgcgct | gttagcgggc | ccattaagtt | ctgtctcggc | gcgtctgcgt | 600 |
| ctggctggct | ggcataaata | tctcactcgc | aatcaaattc | agccgatagc | ggaacgggaa | 660 |
| ggcgactgga | gtgccatgtc | cggttttcaa | caaaccatgc | aaatgctgaa | tgagggcatc | 720 |
| gttcccactg | cgatgctggt | tgccaacgat | cagatggcgc | tgggcgcaat | gcgcgccatt | 780 |
| accgagtccg | ggctgcgcgt | tggtgcggat | atctcggtag | tgggatacga | cgataccgaa | 840 |
| gacagctcat | gttatatccc | gccgttaacc | accatcaaac | aggattttcg | cctgctgggg | 900 |
| caaaccagcg | tggaccgctt | gctgcaactc | tctcagggcc | aggcggtgaa | gggcaatcag | 960 |
| ctgttgcccg | tctcactggt | gaaaagaaaa | accaccctgg | cgcccaatac | gcaaaccgcc | 1020 |
| tctccccgcg | cgttggccga | ttcattaatg | cagctggcac | gacaggtttc | ccgactggaa | 1080 |
| agcgggcaga | gcagcctgag | gcctcctaag | aagaagagga | aggttggatc | cggagcgctg | 1140 |
| ggcatggtag | accgctcacg | gattcttctg | tgtgtcctca | ccttcctgtg | cctctccttt | 1200 |
| aaccccctga | cttccctgct | gcagtgggga | ggggcccacg | actctgacca | gcacccacac | 1260 |
| tcaggctctg | gccgcagtgt | cctgtcattc | gagtcaggtt | ctggggggctg | gtttgactgg | 1320 |
| atgatgccta | ctcttctctt | atggctggta | aatggtgtga | ttgtcctgag | cgtctttgtg | 1380 |
| aagctgctgg | ttcatgggga | gccagtgatc | cggccacact | cgcgctcctc | ggtcaccttc | 1440 |
| tggaggcacc | ggaaacaggc | agatctggat | ctcgccagag | gagattttgc | agctgctgcc | 1500 |
| gccaacctac | aaacctgcct | ggcagttttg | gcccgggcac | tgcccacctc | ccgcctggac | 1560 |
| ctggcctgca | gcctctcctg | gaacgtgatc | cgctacagcc | tgcagaagct | acgcctggtg | 1620 |
| cgctggctgc | tcaagaaagt | cttccagtgc | ggcgggcca | cgccagccac | tgaggcaggc | 1680 |
| tttgaagacg | aagctaagac | cagcgcccgg | gatgcggctc | tggcctatca | ccggctgcac | 1740 |
| cagctgcaca | tcacagggaa | gcttcctgca | ggatccgcct | gttccgatgt | acacatggcg | 1800 |
| ttgtgtgccg | tgaacctggc | tgaatgtgca | gaggagaaga | tcccaccgag | cacactggtt | 1860 |

-continued

```
gagatccatc tgactgctgc catgggctc aagacccggt gtggaggcaa gctgggcttc    1920
ctggccagct acttcctcag ccgagcccag agcctgtgtg ccccgagca cagtgctgtt     1980 cctgactccc tgcgctggct ctgccacccc ctgggccaga agttttcat ggagcggagc     2040 tggtctgtga agtcagctgc aaggagagt ctatactgtg cccagaggaa cccagctgac     2100
cccattgcgc aggtccacca ggccttctgc aagaacctgc tggagcgagc tatagagtcc    2160
ttggtgaaac ctcaggccaa gagaaggct ggagaccagg aagaagagag ctgtgaattc     2220
tccagtgctc tggagtactt gaaattactt cattcttttg tggactctgt gggggttatg    2280 agcccccac tctccaggag ctccgtgctc aagtccgccc tgggtccaga catcatctgt     2340
cggtggtgga cgtctgcaat cactgtggcc atcagctggc tccagggaga cgatgcagct    2400
gtgcgctctc attttaccaa agtggaacgc atccccaagg ccctggaagt gacagagagc    2460
cccctggtga aggccatctt ccatgcctgc agagccatgc atgcctcact ccctgggaaa    2520
gcagatgggc agcagagttc cttctgccat tgcgagaggg ccagtggcca cctatggagc    2580
agcctcaacg tcagtggggg cacctctgac cctgccctca accacgtggt ccagctgctc    2640
acctgtgacc tgctactgtc gctacggaca gcgctctggc aaaaacaggc cagtgccagc    2700
caggctgtgg gggagaccta ccacgcgtca ggcgctgaac tggcgggctt ccaacgggac    2760
ctgggcagcc tgcgcaggct ggcacacagc ttccgcccag cataccgcaa ggtgttcctg    2820
catgaagcca ccgtgcgcct gatggcagga ggcagcccca cccgcaccca ccagctgctg    2880
gaacacagcc tgcggcggcg caccacgcag agcaccaaga cggagaggt ggatgcctgg    2940 cccggccagc gagagcgggc caccgccatc ctgctggcct gccgccacct gcccctctcc    3000
ttcctctcct ccccgggcca gcgggcagtg ctgctggccg aagctgcccg caccctggag    3060
aaggtgggcg accggcgctc ctgcaacgac tgccagcaga tgattgttaa gctgggtggt    3120
ggcactgcca ttgccgcctc ctgactcgag                                     3150
```

<210> SEQ ID NO 6
<211> LENGTH: 1049
<212> TYPE: PRT
<213> ORGANISM: Artificial Sequence
<220> FEATURE:
<223> OTHER INFORMATION: Description of Artificial Sequence:Amino acid
      sequence encoded from KpnI to XhoI in ISRP-LacI
      Fusion Protein

<400> SEQUENCE: 6

```
Gly Thr Thr Met Lys Pro Val Thr Leu Tyr Asp Val Ala Glu Tyr Ala
 1               5                  10                  15

Gly Val Ser Tyr Gln Thr Val Ser Arg Val Val Asn Gln Ala Ser His
            20                  25                  30

Val Ser Ala Lys Thr Arg Glu Lys Val Glu Ala Ala Met Ala Glu Leu
        35                  40                  45

Asn Tyr Ile Pro Asn Arg Val Ala Gln Gln Leu Ala Gly Lys Gln Ser
    50                  55                  60

Leu Leu Ile Gly Val Ala Thr Ser Ser Leu Ala Leu His Ala Pro Ser
65                  70                  75                  80

Gln Ile Val Ala Ala Ile Lys Ser Arg Ala Asp Gln Leu Gly Ala Ser
                85                  90                  95

Val Val Val Ser Met Val Glu Arg Ser Gly Val Glu Ala Cys Lys Ala
            100                 105                 110

Ala Val His Asn Leu Leu Ala Gln Arg Val Ser Gly Leu Ile Ile Asn
        115                 120                 125
```

-continued

```
Tyr Pro Leu Asp Asp Gln Asp Ala Ile Ala Val Glu Ala Ala Cys Thr
    130                 135                 140
Asn Val Pro Ala Leu Phe Leu Asp Val Ser Asp Gln Thr Pro Ile Asn
145                 150                 155                 160
Ser Ile Ile Phe Ser His Glu Asp Gly Thr Arg Leu Gly Val Glu His
                165                 170                 175
Leu Val Ala Leu Gly His Gln Gln Ile Ala Leu Leu Ala Gly Pro Leu
                180                 185                 190
Ser Ser Val Ser Ala Arg Leu Arg Leu Ala Gly Trp His Lys Tyr Leu
            195                 200                 205
Thr Arg Asn Gln Ile Gln Pro Ile Ala Glu Arg Glu Gly Asp Trp Ser
    210                 215                 220
Ala Met Ser Gly Phe Gln Gln Thr Met Gln Met Leu Asn Glu Gly Ile
225                 230                 235                 240
Val Pro Thr Ala Met Leu Val Ala Asn Asp Gln Met Ala Leu Gly Ala
                245                 250                 255
Met Arg Ala Ile Thr Glu Ser Gly Leu Arg Val Gly Ala Asp Ile Ser
                260                 265                 270
Val Val Gly Tyr Asp Asp Thr Glu Asp Ser Ser Cys Tyr Ile Pro Pro
            275                 280                 285
Leu Thr Thr Ile Lys Gln Asp Phe Arg Leu Leu Gly Gln Thr Ser Val
    290                 295                 300
Asp Arg Leu Leu Gln Leu Ser Gln Gly Gln Ala Val Lys Gly Asn Gln
305                 310                 315                 320
Leu Leu Pro Val Ser Leu Val Lys Arg Lys Thr Thr Leu Ala Pro Asn
                325                 330                 335
Thr Gln Thr Ala Ser Pro Arg Ala Leu Ala Asp Ser Leu Met Gln Leu
                340                 345                 350
Ala Arg Gln Val Ser Arg Leu Glu Ser Gly Gln Ser Ser Leu Arg Pro
            355                 360                 365
Pro Lys Lys Lys Arg Lys Val Gly Ser Gly Ala Leu Gly Met Val Asp
    370                 375                 380
Arg Ser Arg Ile Leu Leu Cys Val Leu Thr Phe Leu Cys Leu Ser Phe
385                 390                 395                 400
Asn Pro Leu Thr Ser Leu Leu Gln Trp Gly Gly Ala His Asp Ser Asp
                405                 410                 415
Gln His Pro His Ser Gly Ser Gly Arg Ser Val Leu Ser Phe Glu Ser
                420                 425                 430
Gly Ser Gly Gly Trp Phe Asp Trp Met Met Pro Thr Leu Leu Leu Trp
            435                 440                 445
Leu Val Asn Gly Val Ile Val Leu Ser Val Phe Val Lys Leu Leu Val
    450                 455                 460
His Gly Glu Pro Val Ile Arg Pro His Ser Arg Ser Val Thr Phe
465                 470                 475                 480
Trp Arg His Arg Lys Gln Ala Asp Leu Asp Leu Ala Arg Gly Asp Phe
                485                 490                 495
Ala Ala Ala Ala Ala Asn Leu Gln Thr Cys Leu Ala Val Leu Gly Arg
                500                 505                 510
Ala Leu Pro Thr Ser Arg Leu Asp Leu Ala Cys Ser Leu Ser Trp Asn
            515                 520                 525
Val Ile Arg Tyr Ser Leu Gln Lys Leu Arg Leu Val Arg Trp Leu Leu
    530                 535                 540
```

-continued

```
Lys Lys Val Phe Gln Cys Arg Arg Ala Thr Pro Ala Thr Glu Ala Gly
545                 550                 555                 560

Phe Glu Asp Glu Ala Lys Thr Ser Ala Arg Asp Ala Ala Leu Ala Tyr
                565                 570                 575

His Arg Leu His Gln Leu His Ile Thr Gly Lys Leu Pro Ala Gly Ser
                580                 585                 590

Ala Cys Ser Asp Val His Met Ala Leu Cys Ala Val Asn Leu Ala Glu
            595                 600                 605

Cys Ala Glu Lys Ile Pro Pro Ser Thr Leu Val Glu Ile His Leu
        610                 615                 620

Thr Ala Ala Met Gly Leu Lys Thr Arg Cys Gly Gly Lys Leu Gly Phe
625                 630                 635                 640

Leu Ala Ser Tyr Phe Leu Ser Arg Ala Gln Ser Leu Cys Gly Pro Glu
                645                 650                 655

His Ser Ala Val Pro Asp Ser Leu Arg Trp Leu Cys His Pro Leu Gly
                660                 665                 670

Gln Lys Phe Phe Met Glu Arg Ser Trp Ser Val Lys Ser Ala Ala Lys
            675                 680                 685

Glu Ser Leu Tyr Cys Ala Gln Arg Asn Pro Ala Asp Pro Ile Ala Gln
690                 695                 700

Val His Gln Ala Phe Cys Lys Asn Leu Leu Glu Arg Ala Ile Glu Ser
705                 710                 715                 720

Leu Val Lys Pro Gln Ala Lys Lys Ala Gly Asp Gln Glu Glu
                725                 730                 735

Ser Cys Glu Phe Ser Ser Ala Leu Glu Tyr Leu Lys Leu Leu His Ser
            740                 745                 750

Phe Val Asp Ser Val Gly Val Met Ser Pro Pro Leu Ser Arg Ser Ser
            755                 760                 765

Val Leu Lys Ser Ala Leu Gly Pro Asp Ile Ile Cys Arg Trp Trp Thr
        770                 775                 780

Ser Ala Ile Thr Val Ala Ile Ser Trp Leu Gln Gly Asp Asp Ala Ala
785                 790                 795                 800

Val Arg Ser His Phe Thr Lys Val Glu Arg Ile Pro Lys Ala Leu Glu
                805                 810                 815

Val Thr Glu Ser Pro Leu Val Lys Ala Ile Phe His Ala Cys Arg Ala
                820                 825                 830

Met His Ala Ser Leu Pro Gly Lys Ala Asp Gly Gln Gln Ser Ser Phe
            835                 840                 845

Cys His Cys Glu Arg Ala Ser Gly His Leu Trp Ser Ser Leu Asn Val
850                 855                 860

Ser Gly Gly Thr Ser Asp Pro Ala Leu Asn His Val Val Gln Leu Leu
865                 870                 875                 880

Thr Cys Asp Leu Leu Leu Ser Leu Arg Thr Ala Leu Trp Gln Lys Gln
                885                 890                 895

Ala Ser Ala Ser Gln Ala Val Gly Glu Thr Tyr His Ala Ser Gly Ala
                900                 905                 910

Glu Leu Ala Gly Phe Gln Arg Asp Leu Gly Ser Leu Arg Arg Leu Ala
            915                 920                 925

His Ser Phe Arg Pro Ala Tyr Arg Lys Val Phe Leu His Glu Ala Thr
            930                 935                 940

Val Arg Leu Met Ala Gly Gly Ser Pro Thr Arg Thr His Gln Leu Leu
945                 950                 955                 960
```

```
Glu His Ser Leu Arg Arg Arg Thr Thr Gln Ser Thr Lys His Gly Glu
                965                 970                 975
Val Asp Ala Trp Pro Gly Gln Arg Glu Arg Ala Thr Ala Ile Leu Leu
            980                 985                 990
Ala Cys Arg His Leu Pro Leu Ser Phe Leu Ser Ser Pro Gly Gln Arg
        995                 1000                1005
Ala Val Leu Leu Ala Glu Ala Ala Arg Thr Leu Glu Lys Val Gly Asp
    1010                1015                1020
Arg Arg Ser Cys Asn Asp Cys Gln Gln Met Ile Val Lys Leu Gly Gly
1025                1030                1035                1040
Gly Thr Ala Ile Ala Ala Ser Leu Glu
            1045

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:nuclear
      localization seqiemce

<400> SEQUENCE: 7

Pro Lys Lys Lys Arg Lys Val
 1               5

<210> SEQ ID NO 8
<211> LENGTH: 107
<212> TYPE: DNA
<213> ORGANISM: Artificial Sequence
<220> FEATURE:
<223> OTHER INFORMATION: Description of Artificial Sequence:sequence
      encoding P450 transmembrane/signal sequence.
<220> FEATURE:
<221> NAME/KEY: CDS
<222> LOCATION: (12)..(107)

<400> SEQUENCE: 8
aagcttccac c atg gac cct gtg gtg gtg ctg ggg ctc tgt ctc tcc tgt      50
             Met Asp Pro Val Val Val Leu Gly Leu Cys Leu Ser Cys
               1               5                  10 ttg ctt ctc ctt tca ctc tgg aaa cag agc tat ggg gga ggg aaa ctt      98
Leu Leu Leu Leu Ser Leu Trp Lys Gln Ser Tyr Gly Gly Gly Lys Leu
     15                  20                  25 gga tcc gga                                                         107
Gly Ser Gly
 30

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence:sequence
      encoding P450 transmembrane/signal sequence.

<400> SEQUENCE: 9

Met Asp Pro Val Val Val Leu Gly Leu Cys Leu Ser Cys Leu Leu Leu
 1               5                  10                  15
Leu Ser Leu Trp Lys Gln Ser Tyr Gly Gly Gly Lys Leu Gly Ser Gly
             20                  25                  30

<210> SEQ ID NO 10
<211> LENGTH: 36
<212> TYPE: DNA
```

```
<213> ORGANISM: Artificial Sequence
<220> FEATURE:
<223> OTHER INFORMATION: Description of Artificial Sequence:sequence
      encoding g-s-g linkers and caspase-3 cleavage
      sites
<220> FEATURE:
<221> NAME/KEY: CDS
<222> LOCATION: (1)..(36)

<400> SEQUENCE: 10 gat gaa gtg gac gga tca ggt gat gaa gtg gac gga                    36
Asp Glu Val Asp Gly Ser Gly Asp Glu Val Asp Gly
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:sequence
      encoding g-s-g linkers and caspase-3 cleavage
      sites

<400> SEQUENCE: 11

Asp Glu Val Asp Gly Ser Gly Asp Glu Val Asp Gly
 1               5                  10

<210> SEQ ID NO 12
<211> LENGTH: 32
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 12
gcaagcttcc accatgctgc ccggtttggc ac                                32

<210> SEQ ID NO 13
<211> LENGTH: 30
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 13
gctccggatc ctttcttctt cagcatcacc                                   30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 14
gctccggacc agtaacgtta tacgatgtcg                                   30

<210> SEQ ID NO 15
<211> LENGTH: 32
<212> TYPE: DNA
<213> ORGANISM: Artificial Sequence
<220> FEATURE:
<223> OTHER INFORMATION: Description of Artificial
      Sequence:oligonucleotide
```

```
<400> SEQUENCE: 15
gctctagatc aaaccttcct cttcttctta gg                          32

<210> SEQ ID NO 16
<211> LENGTH: 26
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 16
ctccggagcg ctgggcatgg tagacc                                 26

<210> SEQ ID NO 17
<211> LENGTH: 18
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 17
ggcgagatcc agatctgc                                          18

<210> SEQ ID NO 18
<211> LENGTH: 25
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 18
cggtaccacc atgaaaccag taacg                                  25

<210> SEQ ID NO 19
<211> LENGTH: 31
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 19
ctccggatcc aaccttcctc ttcttcttag g                           31

<210> SEQ ID NO 20
<211> LENGTH: 73
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 20
agcttccacc atgccacggc tcctgacgcc ccttctctgc ctaacgctgc tgcccgcgcg    60
cgccgcaaga ggc                                               73

<210> SEQ ID NO 21
<211> LENGTH: 69
<212> TYPE: DNA
<213> ORGANISM: Artificial Sequence
<220> FEATURE:
<223> OTHER INFORMATION: Description of Artificial
      Sequence:oligonucleotide
```

<400> SEQUENCE: 21
gcctcttgcg gcgcgcgcgg gcagcagcgt taggcagaga aggggcgtca ggagccgtgg    60
catggtgga                                                            69

<210> SEQ ID NO 22
<211> LENGTH: 26
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 22
cagcctcaat attccctaca agatcg                                         26

<210> SEQ ID NO 23
<211> LENGTH: 36
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 23
tcaggtccgg atccgcgctt gcgggacagc agcacc                              36

<210> SEQ ID NO 24
<211> LENGTH: 101
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 24
agcttccacc atggaccctg tggtggtgct ggggctctgt ctctcctgtt tgcttctcct    60
ttcactctgg aaacagagct atggggagg gaaacttgga t                         101

<210> SEQ ID NO 25
<211> LENGTH: 101
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 25
ccggatccaa gtttccctcc cccatagctc tgtttccaga gtgaaaggag aagcaaacag    60
gagagacaga gccccagcac caccacaggg tccatggtgg a                        101

<210> SEQ ID NO 26
<211> LENGTH: 75
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 26
ggatccggag atgaagtgga cggatccgga gatgaagtgg acgatgaagt ggacggatcc    60
ggagatgaag tggac                                                     75

```
<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence:amino acid
      sequence of caspase 3 and peptide linker segment.

<400> SEQUENCE: 27

Gly Ser Gly Asp Glu Val Asp Gly Ser Gly Asp Glu Val Asp Gly Ser
 1               5                  10                  15

Gly

<210> SEQ ID NO 28
<211> LENGTH: 42
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 28
ccggagatga agtggacgga tcaggtgatg aagtggacgg at                              42

<210> SEQ ID NO 29
<211> LENGTH: 42
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 29
ccggatccgt ccacttcatc acctgatccg tccacttcat ct                              42

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence:amino acid
      sequence encompassing Site-1 protease cleavage
      site within SREBP-2

<400> SEQUENCE: 30

Pro His Ser Gly Ser Gly Arg Ser Val Leu Ser Phe Glu
 1               5                  10

<210> SEQ ID NO 31
<211> LENGTH: 5
<212> TYPE: PRT
<213> ORGANISM: Artificial Sequence
<220> FEATURE:
<223> OTHER INFORMATION: Description of Artificial
      Sequence:amino acid sequence within human, hamster SREBP-2
      recognized by Site-1 protease

<400> SEQUENCE: 31

Arg Ser Val Leu Ser
 1               5

<210> SEQ ID NO 32
<211> LENGTH: 4
<212> TYPE: PRT
<213> ORGANISM: Artificial Sequence
```

```
-continued

<220> FEATURE:
<223> OTHER INFORMATION: Description of Artificial Sequence:amino acid
      sequence from SREBP-2 required for cleavage by
      Site-2 protease.

<400> SEQUENCE: 32

Asp Arg Ser Arg
```